(12) United States Patent
Pandolfi et al.

(10) Patent No.: US 11,274,301 B2
(45) Date of Patent: Mar. 15, 2022

(54) MICRO-RNA INHIBITORS AND THEIR USES IN DISEASE

(71) Applicant: BETH ISRAEL DEACONESS MEDICAL CENTER, Boston, MA (US)

(72) Inventors: Pier Paolo Pandolfi, Boston, MA (US); Laura Poliseno, New York, NY (US); Yvonne Tay, Brookline, MA (US); Leonardo Salmena, Brookline, MA (US)

(73) Assignee: BETH ISRAEL DEACONESS MEDICAL CENTER, Boston, MA (US)

( * ) Notice: Subject to any disclaimer, the term of this patent is extended or adjusted under 35 U.S.C. 154(b) by 0 days.

(21) Appl. No.: 15/727,156

(22) Filed: Oct. 6, 2017

(65) Prior Publication Data

US 2018/0073025 A1 Mar. 15, 2018

Related U.S. Application Data

(63) Continuation of application No. 14/111,489, filed as application No. PCT/US2012/033359 on Apr. 12, 2012, now Pat. No. 10,131,905.

(60) Provisional application No. 61/474,593, filed on Apr. 12, 2011.

(51) Int. Cl.
  *C12N 15/11* (2006.01)
  *C12N 15/113* (2010.01)
  *A61K 45/06* (2006.01)

(52) U.S. Cl.
  CPC ............ *C12N 15/113* (2013.01); *A61K 45/06* (2013.01); *C12N 2310/113* (2013.01); *C12N 2310/315* (2013.01); *C12N 2310/321* (2013.01); *C12N 2310/3231* (2013.01); *C12N 2320/30* (2013.01)

(58) Field of Classification Search
  CPC ............ C12N 15/113; C12N 2310/315; C12N 2310/321; C12N 2320/30; C12N 2310/113
  See application file for complete search history.

(56) References Cited

U.S. PATENT DOCUMENTS

| | | |
|---|---|---|
| 2008/0306006 A1 | 12/2008 | Croce et al. |
| 2009/0239818 A1 | 9/2009 | Cheng |
| 2010/0004320 A1 | 1/2010 | Elmen et al. |
| 2010/0035966 A1* | 2/2010 | Linsley .................. C12N 15/111 514/44 A |
| 2010/0035968 A1 | 2/2010 | Rasmussen et al. |
| 2010/0179213 A1* | 7/2010 | Patrawala ............ C12N 15/113 514/44 R |

FOREIGN PATENT DOCUMENTS

| | | | |
|---|---|---|---|
| EP | 2243833 A1 | 10/2010 | |
| WO | WO-2007112754 A2 * | 10/2007 | ........... C12N 15/113 |
| WO | 2009/108860 A2 | 9/2009 | |
| WO | 2010/056737 A2 | 5/2010 | |
| WO | 2010/066384 A1 | 6/2010 | |

OTHER PUBLICATIONS

Moyad et al., Statins, Especially Atorvastatin, May Favorably Influence Clinical Presentation and Biochemical Progression-Free Survival After Brachytherapy for Clinically Localized Prostate Cancer, Urology, 2005, 66: 1150-1154 (Year: 2005).*
Tu et al, MicroRNA-22 Downregulation by Atorvastatin in a Mouse Model of Cardiac Hypertrophy: a new Mechanism for Antihypertrophic Intervention, Cell Physiol Biochem, 2013, 31: 997-1008 (Year: 2013).*
Liu et al, miR-22 functions as a micro-oncogene in transformed human bronchial epithelial cells induced by anti-benzo[a]pyrene-7,8-diol-9,10-epoxide, Toxicology in Vitro, Feb. 17, 2010, 24: 1168-1175 (Year: 2010).*
Hodgson etal, Decreased Expression and Androgen Regulation of the Tumor Suppressor Gene INPP4B in Prostate Cancer, Cancer Research, Jan. 2011,71, 2: 572-582 (Year: 2011).*
Bastola et al, Downregulation of PTEN/MMAC/TEP1 expression in human prostate cancer cell line DU145 by growth stimuli, Mol Cell Biochem, 2002, 236: 75-81 (Year: 2002).*
Zhang et al., MicroRNA-21 (miR-21) represses tumor suppressor PTEN and promotes growth and invasion in non-small cell lung cancer (NSCLC), Clinica Chimica Acta, 411: 846-852 (2010).
Park et al., "Antisense Inhibition of microRNA-21 or -221 Arrests Cell Cycle, Induces Apoptosis, and Sensitizes the Effects of Gemcitabine in Pancreatic Adenocarcinoma," Pancreas, 38: e190-e199 (2009).
Huse et al., "The PTEN-regulating microRNA miR-26a is amplified in high-grade glioma and facilitates gliomagenesis in vivo," Genes and Development, 23:1327-1337 (2009).
Poliseno et al., "Identification of the MiR-106b similar to 25 MicroRNA Cluster as Proto-Oncogene PTEN-Targeting Intron that cooperates with its host gene MCM7 in transformation," Science Signaling, 3: 1-13 (2010).
Fan et al., "MicroRNA-22 promotes cell survival upon UV radiation by repressing PTEN," Biochemical and Biophysical Research Communications, 417: 546-551 (2012).
Lou et al., "MicroRNA-21 promotes the cell proliferation, invasion and migration abilities in ovarian epithelial carcinomas through inhibiting the expression of PTEN protein," International Journal of Molecular Medicine, 26: 819-827 (2010).

(Continued)

*Primary Examiner* — Ekaterina Poliakova-Georgantas
(74) *Attorney, Agent, or Firm* — Morgan, Lewis & Bockius LLP

(57) ABSTRACT

The invention relates to the treatment and prevention of cancer by administering agents that inhibit the activity of microRNAs that modulate tumor suppressor genes, which can include PTEN, p53, and INPP4B, among others. Inhibitors can include oligonucleotides that are at least partially complementary to these miRNAs. In some embodiments, these inhibitors are chemically modified oligonucleotides, including locked nucleic acids (LNAs).

10 Claims, 31 Drawing Sheets

Specification includes a Sequence Listing.

(56) References Cited

OTHER PUBLICATIONS

Wan et al., "Regulation of the transcription factor NF-kB1 by microRNA-9 in human gastric adenocarcinoma," Molecular Cancer, 9: 1-10 (2010).
Laios et al., "Potential role of miR-9 and miR-223 in recurrent ovarian cancer," Molecular Cancer, 7: 1-14 (2008).
Poliseno et al., "A coding-independent function of gene and pseudogene mRNAs regulates tumour biology," Nature, 465: 1033-1038 (2010).
Aigner, "MicroRNAs (miRNAs) in cancer invasion and metastasis: therapeutic approaches based on metastasis-related miRNAs," Journal of Molecular Medicine, 89: 445-457 (2011).
Leslie et al., "Non-genomic loss of PTEN function in cancer: not in my genes," Trends in Pharmacological Sciences, 32: 131-140 (2011).
Ma et al., "miR-9, a MYC/MYCN-activated microRNA, regulates E-cadherin and cancer metastasis," Nature Cell Biology, 12: 247-256 (2010).
International Search Report and Written Opinion issued in International Patent Application No. PCT/US2012/033359 dated Sep. 24, 2012.
Schaefer et al., "Diagnostic and prognostic implications of microRNA profiling in prostate carcinoma," International Journal of Cancer, 126: 1166-1176 (2009).

\* cited by examiner

| ID | Prostate GSE21036 | | PTEN Anti-coexp | | | | Colon GSE18392 | |
|---|---|---|---|---|---|---|---|---|
| | Pval | t | logFC | R2 - all | R2 - CaP | Pval-all | Pval-CaP | Pval | logFC |
| hsa-miR-518c* | 0.00 | -4.24 | -1.58 | 0.08 | 0.07 | 0.00 | 0.003 | 0.04 | -0.14 |

FIGURE 9

| Table 1: List of Regulatory miRNAs ||||||
| --- | --- | --- | --- | --- | --- | --- |
| | MicroRNA ||| Other tumor suppressor targets || Outside 3'UTR targeting |
| Seq ID No. | Family | Name | Sequence | p53 | INPP4B | |
| 1 | 9 | 9 | UCUGCCCCUCCGCUGCUGCCA | Yes | - | Yes |
| 2 | 15 | 15b | UAGCAGCACAUCAUGGUUUACA | - | Yes | - |
| 3 | 17 | 93 | CAAAGUGCUGUUCGUGCAGGUAG | - | Yes | - |
| 4 | 17 | 106a | AAAAGUGCUUACAGUGCAGGUAG | Yes | - | - |
| 5 | 17 | 106b | UAAAGUGCUGACAGUGCAGAU | - | - | - |
| 6 | 17 | 17-5p | CAAAGUGCUUACAGUGCAGGUAG | Yes | - | - |
| 7 | 17 | 20a | UAAAGUGCUUAUAGUGCAGGUAG | Yes | - | - |
| 8 | 17 | 20b | CAAAGUGCUCAUAGUGCAGGUAG | Yes | - | - |
| 9 | 19 | 19a | UGUGCAAAUCUAUGCAAAACUGA | - | - | - |
| 10 | 19 | 19b | UGUGCAAAUCCAUGCAAAACUGA | Yes | - | - |
| 11 | 21 | 21 | UAGCUUAUCAGACUGAUGUUGA | - | Yes | - |
| 12 | 22 | 22 | AAGCUGCCAGUUGAAGAACUGU | - | Yes | - |
| 13 | 23 | 23a | AUCACAUUGCCAGGGAUUUCC | Yes | - | Yes |
| 14 | 23 | 23b | AUCACAUUGCCAGGGAUUACC | - | - | - |
| 15 | 25 | 25 | CAUUGCACUUGUCUCGGUCUGA | - | - | - |
| 16 | 25 | 92a | UAUUGCACUUGUCCCGGCCUGU | - | Yes | - |
| 17 | 25 | 92b | UAUUGCACUCGUCCCGGCCUCC | - | Yes | - |
| 18 | 26 | 26a | UUCAAGUAAUCCAGGAUAGGCU | Yes | - | - |
| 19 | 32 | 32 | UAUUGCACAUUACUAAGUUGCA | - | Yes | - |
| 20 | 136 | 136 | ACUCCAUUUGUUUUGAUGAUGGA | - | - | - |
| 21 | 8 | 141 | UAACACUGUCUGGUAAAGAUGG | - | - | - |
| 22 | 144 | 144 | UACAGUAUAGAUGAUGUACU | - | - | - |
| 23 | 182 | 182 | UUUGGCAAUGGUAGAACUCACACU | - | Yes | - |
| 24 | 193 | 193b | AACUGGCCCUCAAAGUCCCGCU | - | - | - |
| 25 | 205 | 205 | UCCUUCAUUCCACCGGAGUCUG | Yes | Yes | - |
| 26 | 214 | 214 | ACAGCAGGCACAGACAGGCAGU | - | - | - |
| 27 | 216 | 216a | UAAUCUCAGCUGGCAACUGUGA | Yes | - | - |
| 28 | 217 | 217 | UACUGCAUCAGGAACUGAUUGGA | - | - | - |
| 29 | 221 | 221 | AGCUACAUUGUCUGCUGGGUUUC | - | Yes | - |
| 30 | 221 | 222 | AGCUACAUCUGGCUACUGGGU | - | - | - |
| 31 | 302 | 302a | UAAGUGCUUCCAUGUUUUGGUGA | - | Yes | - |
| 32 | 302 | 302b | UAAGUGCUUCCAUGUUUUAGUAG | - | Yes | - |
| 33 | 302 | 302c | UAAGUGCUUCCAUGUUUCAGUGG | Yes | Yes | - |
| 34 | 302 | 302d | UAAGUGCUUCCAUGUUUGAGUGU | Yes | Yes | - |
| 35 | 302 | 302e | UAAGUGCUUCCAUGCUU | Yes | - | - |
| 36 | 302 | 302f | UAAUUGCUUCCAUGUUU | - | - | - |
| 37 | 330 | 330-5p | UCUCUGGGCCUGUGUCUUAGGC | Yes | Yes | Yes |
| 38 | 363 | 363 | AAUUGCACGGUAUCCAUCUGUA | - | Yes | - |

FIGURE 9 continued

| | | | | | | |
|---|---|---|---|---|---|---|
| 39 | 367 | 367 | AAUUGCACUUUAGCAAUGGUGA | - | Yes | - |
| 40 | 290 | 372 | AAAGUGCUGCGACAUUUGAGCGU | - | Yes | - |
| 41 | 373 | 373 | GAAGUGCUUCGAUUUUGGGGUGU | - | Yes | - |
| 42 | 375 | 375 | UUUGUUCGUUCGGCUCGCGUGA | Yes | Yes | - |
| 43 | 486 | 486 | UCCUGUACUGAGCUGCCCCGAG | - | Yes | - |
| 44 | 154 | 494 | UGAAACAUACACGGGAAACCUC | - | - | - |
| 45 | 506 | 512-3p | AAGUGCUGUCAUAGCUGAGGUC | Yes | Yes | - |
| 46 | 515 | 518c* | UCUCUGGAGGGAAGCACUUUCUG | Yes | Yes | Yes |
| 47 | 515 | 518e | AAAGCGCUUCCCUUCAGAGUG | - | - | - |
| 48 | 515 | 519a | AAAGUGCAUCCUUUUAGAGUGU | Yes | Yes | - |
| 49 | 515 | 519b-3p | AAAGUGCAUCCUUUUAGAGGUU | - | Yes | - |
| 50 | 515 | 519c | CUCUAGAGGGAAGCGCUUUCUG | - | - | - |
| 51 | 515 | 519d | CAAAGUGCCUCCCUUUAGAGUG | - | - | - |
| 52 | 515 | 520a | CUCCAGAGGGAAGUACUUUCU | - | - | - |
| 53 | 515 | 520b | AAAGUGCUUCCUUUUAGAGGG | - | Yes | - |
| 54 | 515 | 520c | CUCUAGAGGGAAGCACUUUCUG | - | - | - |
| 55 | 515 | 520d | CUACAAAGGGAAGCCCUUUC | - | - | - |
| 56 | 515 | 520e | AAAGUGCUUCCUUUUUGAGGG | - | Yes | - |
| 57 | 550 | 550a | AGUGCCUGAGGGAGUAAGAGCCC | - | Yes | Yes |
| 58 | 625 | 625 | AGGGGGAAAGUUCUAUAGUCC | Yes | Yes | - |
| 59 | 659 | 659 | CUUGGUUCAGGGAGGGUCCCCA | Yes | Yes | Yes |
| 60 | 663 | 663 | AGGCGGGGCGCCGCGGGACCGC | Yes | Yes | Yes |
| 61 | 671 | 671-5p | AGGAAGCCCUGGAGGGGCUGGAG | Yes | Yes | Yes |
| 62 | 760 | 760 | CGGCUCUGGGUCUGUGGGGA | Yes | Yes | Yes |
| 63 | 877 | 877 | GUAGAGGAGAUGGCGCAGGG | - | Yes | Yes |
| 64 | 1225 | 1225-5p | GUGGGUACGGCCCAGUGGGGG | Yes | Yes | Yes |
| 65 | 1299 | 1299 | UUCUGGAAUUCUGUGUGAGGGA | Yes | Yes | Yes |
| 66 | 1913 | 1913 | UCUGCCCCUCCGCUGCUGCCA | Yes | - | Yes |
| 67 | | 23a* | GGGGUUCCUGGGGAUGGGAUUU | | | |

SEQUENCE LISTING

```
<160> NUMBER OF SEQ ID NOS: 67

<210> SEQ ID NO 1
<211> LENGTH: 22
<212> TYPE: RNA
<213> ORGANISM: Homo sapiens

<400> SEQUENCE: 1
ucugcccccu ccgcugcugc ca                                          22

<210> SEQ ID NO 2
<211> LENGTH: 22
<212> TYPE: RNA
<213> ORGANISM: Homo sapiens

<400> SEQUENCE: 2
uagcagcaca ucaugguuua ca                                          22

<210> SEQ ID NO 3
<211> LENGTH: 23
<212> TYPE: RNA
<213> ORGANISM: Homo sapiens

<400> SEQUENCE: 3
caaagugcug uucgugcagg uag                                         23

<210> SEQ ID NO 4
<211> LENGTH: 23
<212> TYPE: RNA
<213> ORGANISM: Homo sapiens

<400> SEQUENCE: 4
aaaagugcuu acagugcagg uag                                         23

<210> SEQ ID NO 5
<211> LENGTH: 21
<212> TYPE: RNA
<213> ORGANISM: Homo sapiens

<400> SEQUENCE: 5
uaaagugcug acagugcaga u                                           21

<210> SEQ ID NO 6
<211> LENGTH: 23
<212> TYPE: RNA
<213> ORGANISM: Homo sapiens

<400> SEQUENCE: 6
caaagugcuu acagugcagg uag                                         23
```

```
<210> SEQ ID NO 7
<211> LENGTH: 23
<212> TYPE: RNA
<213> ORGANISM: Homo sapiens

<400> SEQUENCE: 7
uaaagugcuu auagugcagg uag                                              23

<210> SEQ ID NO 8
<211> LENGTH: 23
<212> TYPE: RNA
<213> ORGANISM: Homo sapiens

<400> SEQUENCE: 8
caaagugcuc auagugcagg uag                                              23

<210> SEQ ID NO 9
<211> LENGTH: 23
<212> TYPE: RNA
<213> ORGANISM: Homo sapiens

<400> SEQUENCE: 9
ugugcaaauc uaugcaaaac uga                                              23

<210> SEQ ID NO 10
<211> LENGTH: 23
<212> TYPE: RNA
<213> ORGANISM: Homo sapiens

<400> SEQUENCE: 10
ugugcaaauc caugcaaaac uga                                              23

<210> SEQ ID NO 11
<211> LENGTH: 22
<212> TYPE: RNA
<213> ORGANISM: Homo sapiens

<400> SEQUENCE: 11
uagcuuauca gacugauguu ga                                               22

<210> SEQ ID NO 12
<211> LENGTH: 22
<212> TYPE: RNA
<213> ORGANISM: Homo sapiens

<400> SEQUENCE: 12
aagcugccag uugaagaacu gu                                               22

<210> SEQ ID NO 13
<211> LENGTH: 21
<212> TYPE: RNA
<213> ORGANISM: Homo sapiens

<400> SEQUENCE: 13
aucacauugc cagggauuuc c                                                21

<210> SEQ ID NO 14
<211> LENGTH: 21
<212> TYPE: RNA
<213> ORGANISM: Homo sapiens

<400> SEQUENCE: 14
aucacauugc cagggauuac c                                                21
```

```
<210> SEQ ID NO 15
<211> LENGTH: 22
<212> TYPE: RNA
<213> ORGANISM: Homo sapiens

<400> SEQUENCE: 15
cauugcacuu gucucggucu ga                                              22

<210> SEQ ID NO 16
<211> LENGTH: 22
<212> TYPE: RNA
<213> ORGANISM: Homo sapiens

<400> SEQUENCE: 16
uauugcacuu gucccggccu gu                                              22

<210> SEQ ID NO 17
<211> LENGTH: 22
<212> TYPE: RNA
<213> ORGANISM: Homo sapiens

<400> SEQUENCE: 17
uauugcacuc gucccggccu cc                                              22

<210> SEQ ID NO 18
<211> LENGTH: 22
<212> TYPE: RNA
<213> ORGANISM: Homo sapiens

<400> SEQUENCE: 18
uucaaguaau ccaggauagg cu                                              22

<210> SEQ ID NO 19
<211> LENGTH: 22
<212> TYPE: RNA
<213> ORGANISM: Homo sapiens

<400> SEQUENCE: 19
uauugcacau uacuaaguug ca                                              22

<210> SEQ ID NO 20
<211> LENGTH: 23
<212> TYPE: RNA
<213> ORGANISM: Homo sapiens

<400> SEQUENCE: 20
acuccauuug uuuugaugau gga                                             23

<210> SEQ ID NO 21
<211> LENGTH: 22
<212> TYPE: RNA
<213> ORGANISM: Homo sapiens

<400> SEQUENCE: 21
uaacacuguc ugguaaagau gg                                              22

<210> SEQ ID NO 22
<211> LENGTH: 20
<212> TYPE: RNA
<213> ORGANISM: Homo sapiens

<400> SEQUENCE: 22
uacaguauag augauguacu                                                 20
```

```
<210> SEQ ID NO 23
<211> LENGTH: 24
<212> TYPE: RNA
<213> ORGANISM: Homo sapiens

<400> SEQUENCE: 23
uuuggcaaug guagaacuca cacu                                              24

<210> SEQ ID NO 24
<211> LENGTH: 22
<212> TYPE: RNA
<213> ORGANISM: Homo sapiens

<400> SEQUENCE: 24
aacuggcccu caaagucccg cu                                                22

<210> SEQ ID NO 25
<211> LENGTH: 22
<212> TYPE: RNA
<213> ORGANISM: Homo sapiens

<400> SEQUENCE: 25
uccuucauuc caccggaguc ug                                                22

<210> SEQ ID NO 26
<211> LENGTH: 22
<212> TYPE: RNA
<213> ORGANISM: Homo sapiens

<400> SEQUENCE: 26
acagcaggca cagacaggca gu                                                22

<210> SEQ ID NO 27
<211> LENGTH: 22
<212> TYPE: RNA
<213> ORGANISM: Homo sapiens

<400> SEQUENCE: 27
uaaucucagc uggcaacugu ga                                                22

<210> SEQ ID NO 28
<211> LENGTH: 23
<212> TYPE: RNA
<213> ORGANISM: Homo sapiens

<400> SEQUENCE: 28
uacugcauca ggaacugauu gga                                               23

<210> SEQ ID NO 29
<211> LENGTH: 23
<212> TYPE: RNA
<213> ORGANISM: Homo sapiens

<400> SEQUENCE: 29
agcuacauug ucugcugggu uuc                                               23

<210> SEQ ID NO 30
<211> LENGTH: 21
<212> TYPE: RNA
<213> ORGANISM: Homo sapiens

<400> SEQUENCE: 30
agcuacaucu ggcuacuggg u                                                 21
```

```
<210> SEQ ID NO 31
<211> LENGTH: 23
<212> TYPE: RNA
<213> ORGANISM: Homo sapiens

<400> SEQUENCE: 31
uaagugcuuc cauguuuugg uga                                              23

<210> SEQ ID NO 32
<211> LENGTH: 23
<212> TYPE: RNA
<213> ORGANISM: Homo sapiens

<400> SEQUENCE: 32
uaagugcuuc cauguuuag uag                                               23

<210> SEQ ID NO 33
<211> LENGTH: 23
<212> TYPE: RNA
<213> ORGANISM: Homo sapiens

<400> SEQUENCE: 33
uaagugcuuc cauguuucag ugg                                              23

<210> SEQ ID NO 34
<211> LENGTH: 23
<212> TYPE: RNA
<213> ORGANISM: Homo sapiens

<400> SEQUENCE: 34
uaagugcuuc cauguuugag ugu                                              23

<210> SEQ ID NO 35
<211> LENGTH: 17
<212> TYPE: RNA
<213> ORGANISM: Homo sapiens

<400> SEQUENCE: 35
uaagugcuuc caugcuu                                                     17

<210> SEQ ID NO 36
<211> LENGTH: 17
<212> TYPE: RNA
<213> ORGANISM: Homo sapiens

<400> SEQUENCE: 36
uaauugcuuc cauguuu                                                     17

<210> SEQ ID NO 37
<211> LENGTH: 22
<212> TYPE: RNA
<213> ORGANISM: Homo sapiens

<400> SEQUENCE: 37
ucucugggcc ugugucuuag gc                                               22

<210> SEQ ID NO 38
<211> LENGTH: 22
<212> TYPE: RNA
<213> ORGANISM: Homo sapiens

<400> SEQUENCE: 38
aauugcacgg uauccaucug ua                                               22
```

```
<210> SEQ ID NO 39
<211> LENGTH: 22
<212> TYPE: RNA
<213> ORGANISM: Homo sapiens

<400> SEQUENCE: 39
aauugcacuu uagcaauggu ga                                              22

<210> SEQ ID NO 40
<211> LENGTH: 23
<212> TYPE: RNA
<213> ORGANISM: Homo sapiens

<400> SEQUENCE: 40
aaagugcugc gacauuugag cgu                                             23

<210> SEQ ID NO 41
<211> LENGTH: 23
<212> TYPE: RNA
<213> ORGANISM: Homo sapiens

<400> SEQUENCE: 41
gaagugcuuc gauuuugggg ugu                                             23

<210> SEQ ID NO 42
<211> LENGTH: 22
<212> TYPE: RNA
<213> ORGANISM: Homo sapiens

<400> SEQUENCE: 42
uuuguucguu cggcucgcgu ga                                              22

<210> SEQ ID NO 43
<211> LENGTH: 22
<212> TYPE: RNA
<213> ORGANISM: Homo sapiens

<400> SEQUENCE: 43
uccuguacug agcugccccg ag                                              22

<210> SEQ ID NO 44
<211> LENGTH: 22
<212> TYPE: RNA
<213> ORGANISM: Homo sapiens

<400> SEQUENCE: 44
ugaaacauac acgggaaacc uc                                              22

<210> SEQ ID NO 45
<211> LENGTH: 22
<212> TYPE: RNA
<213> ORGANISM: Homo sapiens

<400> SEQUENCE: 45
aagugcuguc auagcugagg uc                                              22

<210> SEQ ID NO 46
<211> LENGTH: 23
<212> TYPE: RNA
<213> ORGANISM: Homo sapiens

<400> SEQUENCE: 46
ucucuggagg gaagcacuuu cug                                             23
```

```
<210> SEQ ID NO 47
<211> LENGTH: 21
<212> TYPE: RNA
<213> ORGANISM: Homo sapiens

<400> SEQUENCE: 47
aaagcgcuuc ccuucagagu g                                              21

<210> SEQ ID NO 48
<211> LENGTH: 22
<212> TYPE: RNA
<213> ORGANISM: Homo sapiens

<400> SEQUENCE: 48
aaagugcauc cuuuuagagu gu                                             22

<210> SEQ ID NO 49
<211> LENGTH: 22
<212> TYPE: RNA
<213> ORGANISM: Homo sapiens

<400> SEQUENCE: 49
aaagugcauc cuuuuagagg uu                                             22

<210> SEQ ID NO 50
<211> LENGTH: 22
<212> TYPE: RNA
<213> ORGANISM: Homo sapiens

<400> SEQUENCE: 50
cucuagaggg aagcgcuuuc ug                                             22

<210> SEQ ID NO 51
<211> LENGTH: 22
<212> TYPE: RNA
<213> ORGANISM: Homo sapiens

<400> SEQUENCE: 51
caaagugccu cccuuuagag ug                                             22

<210> SEQ ID NO 52
<211> LENGTH: 21
<212> TYPE: RNA
<213> ORGANISM: Homo sapiens

<400> SEQUENCE: 52
cuccagaggg aaguacuuuc u                                              21

<210> SEQ ID NO 53
<211> LENGTH: 21
<212> TYPE: RNA
<213> ORGANISM: Homo sapiens

<400> SEQUENCE: 53
aaagugcuuc cuuuuagagg g                                              21

<210> SEQ ID NO 54
<211> LENGTH: 22
<212> TYPE: RNA
<213> ORGANISM: Homo sapiens

<400> SEQUENCE: 54
cucuagaggg aagcacuuuc ug                                             22
```

```
<210> SEQ ID NO 55
<211> LENGTH: 20
<212> TYPE: RNA
<213> ORGANISM: Homo sapiens

<400> SEQUENCE: 55
cuacaaaggg aagcccuuuc                                              20

<210> SEQ ID NO 56
<211> LENGTH: 21
<212> TYPE: RNA
<213> ORGANISM: Homo sapiens

<400> SEQUENCE: 56
aaagugcuuc cuuuuugagg g                                            21

<210> SEQ ID NO 57
<211> LENGTH: 23
<212> TYPE: RNA
<213> ORGANISM: Homo sapiens

<400> SEQUENCE: 57
agugccugag ggaguaagag ccc                                          23

<210> SEQ ID NO 58
<211> LENGTH: 21
<212> TYPE: RNA
<213> ORGANISM: Homo sapiens

<400> SEQUENCE: 58 aggggggaaag uucuauaguc c                                           21

<210> SEQ ID NO 59
<211> LENGTH: 22
<212> TYPE: RNA
<213> ORGANISM: Homo sapiens

<400> SEQUENCE: 59
cuugguucag ggaggguccc ca                                           22

<210> SEQ ID NO 60
<211> LENGTH: 22
<212> TYPE: RNA
<213> ORGANISM: Homo sapiens

<400> SEQUENCE: 60
aggcggggcg ccgcgggacc gc                                           22

<210> SEQ ID NO 61
<211> LENGTH: 23
<212> TYPE: RNA
<213> ORGANISM: Homo sapiens

<400> SEQUENCE: 61
aggaagcccu ggaggggcug gag                                          23

<210> SEQ ID NO 62
<211> LENGTH: 20
<212> TYPE: RNA
<213> ORGANISM: Homo sapiens

<400> SEQUENCE: 62
cggcucuggg ucuguggga                                               20
```

```
<210> SEQ ID NO 63
<211> LENGTH: 20
<212> TYPE: RNA
<213> ORGANISM: Homo sapiens

<400> SEQUENCE: 63
guagaggaga uggcgcaggg                                                    20

<210> SEQ ID NO 64
<211> LENGTH: 22
<212> TYPE: RNA
<213> ORGANISM: Homo sapiens

<400> SEQUENCE: 64
guggguacgg cccagugggg gg                                                 22

<210> SEQ ID NO 65
<211> LENGTH: 22
<212> TYPE: RNA
<213> ORGANISM: Homo sapiens

<400> SEQUENCE: 65
uucuggaauu cugugugagg ga                                                 22

<210> SEQ ID NO 66
<211> LENGTH: 22
<212> TYPE: RNA
<213> ORGANISM: Homo sapiens

<400> SEQUENCE: 66
ucugcccccu ccgcugcugc ca                                                 22

<210> SEQ ID NO 67
<211> LENGTH: 22
<212> TYPE: RNA
<213> ORGANISM: Homo sapiens

<400> SEQUENCE: 67
gggguuccug gggaugggau uu                                                 22
```

MICRO-RNA INHIBITORS AND THEIR USES IN DISEASE

CROSS REFERENCE TO RELATED APPLICATIONS

This is a continuation application of Ser. No. 14/111,489, filed Jan. 21, 2014 which is a 371 National Stage of International Patent Application No. PCT/US2012/033359, filed on Apr. 12, 2012, which claims the benefit of U.S. Patent Application No. 61/474,593, filed Apr. 12, 2011, the contents of all of which are incorporated herein by reference.

GOVERNMENT SUPPORT

This invention was made with government support under grant number CA082328 awarded by the National Institutes of Health. The government has certain rights in this invention.

SEQUENCE LISTING SUBMISSION VIA EFS-WEB

A computer readable text file, entitled "SequenceListing.txt," created on or about Oct. 6, 2017 with a file size of about 11 kb contains the sequence listing for this application and is hereby incorporated by reference in its entirety.

FIELD OF THE INVENTION

The present invention relates to the treatment and prevention of cancer by administering agents that modulate the activity or expression of microRNAs. Specifically, the invention, in part, provides methods for treating or preventing cancers by inhibiting the expression and/or activity of oncogenic microRNAs that negatively regulate tumor suppressor genes.

BACKGROUND OF THE INVENTION

MicroRNAs (miRNA or miR) are short (usually 18-24 nucleotides) nucleic acid molecules that are able to regulate the expression of target genes. See review by Carrington et al. *Science*, Vol. 301(5631):336-338, 2003). MiRNAs act as repressors of target mRNAs by promoting their degradation, when their sequences are perfectly complementary, and/or by inhibiting translation, when their sequences contain mismatches.

Without being bound by theory, mature miRNAs are believed to be generated by RNA polymerase II (pol II) or RNA polymerase III (pol III; see Qi et al. (2006) *Cellular & Molecular Immunology*, Vol. 3:411-419) and arise from initial transcripts termed primary miRNA transcripts (pri-miRNAs). These pri-miRNAs are frequently several thousand bases long and are therefore processed to make the much shorter mature miRNAs. This processing is believed to occur in two steps. First, pri-miRNAs are processed in the nucleus by the RNase Drosha into about 70- to about 100-nucleotide hairpin-shaped precursors (pre-miRNAs). Second, after transposition to the cytoplasm, the hairpin pre-miRNAs are further processed by the RNase Dicer to produce a double-stranded miRNA. A mature miRNA strand is then incorporated into the RNA-induced silencing complex (RISC), where it associates with its target mRNA by base-pair complementarity and leads to suppression of protein expression.

Cancer is a group of diseases characterized by uncontrolled cell division which can lead to abnormal tissue and, in turn, disruption of normal physiologic processes and, possibly, death. Cancers likely have etiologies in genetic and environmental factors. Regarding the former, cancer-critical genes can be roughly classified into two groups based on whether mutations in them cause loss of function or gain of function outcomes. Loss-of-function mutations of tumor suppressor genes relieve cells of inhibitions that normally help to hold their numbers in check, while gain-of-function mutations of proto-oncogenes stimulate cells to increase their numbers when they should not. Notable tumor suppressor genes include PTEN (phosphatase and tensin homolog), p53 (protein 53 or tumor protein 53), and INPP4B (inositol polyphosphate 4-phosphatase type II). One mechanism by which these genes can be suppressed, and thus lose their ability to suppress the onset of tumorigenesis, is through the binding of their mRNA transcripts and the inhibition of translation.

As the reduction or loss of these genes is linked to cancer development, there is a need in the art for treatment methods that can up-regulate them. Specifically, there is a need for inhibitors that target miRNAs that bind to tumor suppressor genes. Further, the art lacks in inhibitors designed to this end which can be produced cheaply, delivered effectively, and which display adequate bioavailability.

SUMMARY OF THE INVENTION

Accordingly, the present invention is based, in part, on the discovery that a variety of previously unstudied miRNAs regulate tumor suppressor genes, including PTEN and/or p53 and/or INPP4B and that these regulators can be inhibited by administration of nucleic acids that bind to them. For instance, such inhibition could be mediated by sequence specific chemically modified oligonucleotides. An exemplary modification is a locked nucleic acid (LNA) in which the nucleic acid's ribose moiety is modified with an extra bridge connecting the 2' oxygen and 4' carbon, which locks the ribose in the 3'-endo conformation. These LNA inhibitors, among others, when directed at the tumor suppressor gene-regulating miRNAs disclosed herein, provide for cost effective anti-cancer agents that can be delivered efficiently and possess sufficient bioavailability for the treatment and prevention of various cancers.

In one aspect, the present invention includes a method of treating or preventing cancer in a subject in need thereof comprising administering to the subject an inhibitor of miRNA, wherein the miRNA is a PTEN regulator.

In some aspects the expression and/or activity of an miRNA that is a PTEN regulator is reduced in the subject following administration of the inhibitor.

In some aspects, the miRNA is selected from a group consisting of: pri-, pre-, duplex, mature, and minor (*) forms.

A PTEN regulator miRNA included in and targeted by the methods of the present invention can be selected from a group consisting of miR-9 (SEQ ID NO: 1), miR-15b (SEQ ID NO: 2), miR-93 (SEQ ID NO: 3), miR-106a (SEQ ID NO: 4), miR-106b (SEQ ID NO: 5), miR-17-5p (SEQ ID NO: 6), miR-20a (SEQ ID NO: 7), miR-20b (SEQ ID NO: 8), miR-19a (SEQ ID NO: 9), miR-19b (SEQ ID NO: 10), miR-21 (SEQ ID NO: 11), miR-22 (SEQ ID NO: 12), miR-23a (SEQ ID NO: 13), miR-23b (SEQ ID NO: 14), miR-25 (SEQ ID NO: 15), miR-92a (SEQ ID NO: 16), miR-92b (SEQ ID NO: 17), miR-26a (SEQ ID NO: 18), miR-32 (SEQ ID NO: 19), miR-136 (SEQ ID NO: 20), miR-141 (SEQ ID NO: 21), miR-144 (SEQ ID NO: 22), miR-182 (SEQ ID NO: 23), miR-193b (SEQ ID NO: 24), miR-205 (SEQ ID NO: 25), miR-214 (SEQ ID NO: 26), miR-216a (SEQ ID NO: 27), miR-217 (SEQ ID NO: 28), miR-221 (SEQ ID NO: 29), miR-222 (SEQ ID NO: 30), miR-302a (SEQ ID NO: 31), miR-302b (SEQ ID NO: 32), miR-302c (SEQ ID NO: 33), miR-302d (SEQ ID NO: 34), miR-302e (SEQ ID NO: 35), miR-302f (SEQ ID NO: 36), miR-330-5p (SEQ ID NO: 37), miR-363 (SEQ ID NO: 38), miR-367 (SEQ ID NO: 39), miR-372 (SEQ ID NO: 40), miR-373 (SEQ ID NO: 41), miR-375 (SEQ ID NO: 42), miR-486 (SEQ ID NO: 43), miR-494 (SEQ ID NO: 44), miR-512-3p (SEQ ID NO: 45), miR-518c* (SEQ ID NO: 46), miR-518e (SEQ ID NO: 47), miR-519a (SEQ ID NO: 48), miR-519b-3p (SEQ ID NO: 49), miR-519c (SEQ ID NO: 50), miR-519d (SEQ ID NO: 51), miR-520a (SEQ ID NO: 52), miR-520b (SEQ ID NO: 53), miR-520c (SEQ ID NO: 54), miR-520d (SEQ ID NO: 55), miR-520e (SEQ ID NO: 56), miR-550a (SEQ ID NO: 57), miR-625 (SEQ ID NO: 58), miR-659 (SEQ ID NO: 59), miR-663 (SEQ ID NO: 60), miR-671-5p (SEQ ID NO: 61), miR-760 (SEQ ID NO: 62), miR-877 (SEQ ID NO: 63), miR-1225-5p (SEQ ID NO: 64), miR-1299 (SEQ ID NO: 65), miR-1913 (SEQ ID NO: 66) and miR-23* (SEQ ID NO:67).

The invention also includes PTEN-targeting miRNAs that also target p53 and/or INPP4B. Also, the miRNAs can target PTEN and/or p53 and/or INPP4B within and/or outside of their 3' untranslated regions (UTRs). Another aspect of the invention includes regulatory miRNAs that bind up to 2, up to 4, up to 6, up to 8, or up to 10 sites of PTEN and/or p53 and/or INPP4B.

In certain aspects, the present invention encompasses inhibition of an miRNA targeting a tumor suppressor gene. In one aspect of the present invention the inhibitor is an antisense oligonucleotide. In another aspect of the present invention, the inhibitor can include a nucleotide sequence that is at least partially complementary to the mature sequence of the miRNA.

In one aspect, the invention comprises inhibitors that are at least partially complementary to the miRNAs described above and herein.

Some aspects of the present invention include chemically modified inhibitors. In certain aspects, the chemical modification is selected from a group consisting of LNA, phosphorothioate, 2'-O-Methyl, and 2'-O-Methoxyethyl. In other aspects, the LNA comprises about 16 or fewer nucleotides. The LNA can also comprise about 7-8 nucleotides.

Another aspect of the present invention is a method of treating or preventing cancer in which the inhibitor is selected based on the tissue environment of the cancer.

In yet another aspect of the present invention, a method of treating cancer is imagined in which the cancer is selected from a variety of cancer types.

The invention also includes methods of treating or preventing cancer in which the subject is a mammal. The invention also includes instances in which the mammal is a human.

One aspect of the present invention is a method of treating or preventing cancer in a subject in need thereof comprising administering to the subject: a first inhibitor of a first miRNA, wherein the miRNA is a PTEN regulator and a second inhibitor of a second miRNA, wherein the miRNA is a p53 regulator or an INPP4B regulator, wherein said first and second inhibitors may be administered in either order or concurrently.

Another aspect of the present invention is a method of treating cancer in a subject in need thereof comprising administering to the subject a first agent that is or comprises an inhibitor of at least one miRNA, wherein the miRNA is a PTEN regulator and a second agent that is or comprises at least one other cancer biologic, therapeutic, chemotherapeutic or drug, wherein said second agent acts at a non-PTEN target or pathway in cells of said cancer, wherein said first and second agents may be administered in either order or concurrently.

Another aspect of the present invention is a pharmaceutical composition comprising an inhibitor of an miRNA that regulates PTEN and/or p53 and/or INPP4B and a pharmaceutically acceptable carrier.

BRIEF DESCRIPTION OF THE DRAWINGS

Table 1 shows a listing of miRNAs studied in the present invention. While this table shows mature and minor sequences, the invention is not limited as such (by way of non-limiting example, it could include pri-, pre-, duplex, mature, and minor (*) forms of the microRNA).

FIG. 1A shows the reduction of PTEN protein levels while FIG. 1B shows the reduction of PTEN mRNA levels. FIGS. 1C and 1D show functional determinations of PTEN reduction, i.e., increased PIP3 and increased Akt phosphorylation. FIG. 1E shows a verification of direct interactions between oncogenic miRNAs and PTEN. FIG. 1F shows a selected group of miRNAs that regulate PTEN, p53, INPP4B, and combinations thereof.

FIG. 2A-FIG. 2C show this overexpression for a variety of miRNAs in a panel of cell lines. FIG. 2D shows this overexpression in primary tumor tissues.

FIG. 3A shows immunohistochemistry (IHC) of scored tissues while FIG. 3B shows quatitation of Dicer abundance by tissue class.

FIG. 4A shows a reduction of PTEN abundance and activity in vitro. FIG. 4B shows an increase in cell growth with miR-22 regulation of PTEN.

FIG. 4C shows that the miR22 effects depend on PTEN. In vivo effects of miRNA regulation of PTEN are seen in FIGS. 4D and 4E.

FIG. 7A-FIG. 7G show various characterizations of miR-518c*. FIG. 7A shows Western blot analysis demonstrating that overexpression of miR-518c* results in a significant decrease in PTEN protein levels in certain cancer cells (NC is negative control and is the bottom dataset in the graph). In FIG. 7C, 518c* is the middle curve while siPTEN 15 the top curve. FIG. 7B shows Luciferase reporter assays demonstrating that overexpression of miR-518c* results in a significant decrease in the activity of PTEN 5'UTR-luciferase (5'UTR-luc; left bar in each set), Luciferase-PTEN CDS (Luc-CDS; center bar in each set) and Luciferase-PTEN 3'UTR (Luc-3'UTR; right bar in each set) reporters (CTL is negative control). FIG. 7C shows Western blot analysis demonstrating that overexpression of miR-518c* results in a significant decrease in p53 protein levels (NC is negative control). FIG. 7D shows Luciferase reporter assays demonstrating that overexpression of miR-518c* results in a significant decrease in activity of the p53-responsive PIG-luciferase (left bar in each set) and p21-luciferase reporters (right bar in each set) (NC is negative control). FIG. 7E shows Western blot analysis demonstrating that overexpression of miR-518c* results in a significant decrease in protein levels of the PTEN ceRNAs VAPA and Zeb2 and a concomitant increase in the protein levels of Phospho-Akt (NC is negative control). FIG. 7F shows proliferation assays demonstrated that overexpression of miR-518c* results in a significant increase in proliferation of DU145 prostate cancer cells (NC is negative control). FIG. 7G shows that miR-518c* expression levels are elevated in selected cancer samples.

FIG. 9 shows Table 1 which includes a listing of miRNAs studied in the present disclosure. While this table shows mature and minor sequences, the invention is not limited as such (by way of non-limiting example, it could include pri-, pre-, duplex, mature, and minor (*) forms of the microRNA).

DETAILED DESCRIPTION OF THE INVENTION

Figure 1A:
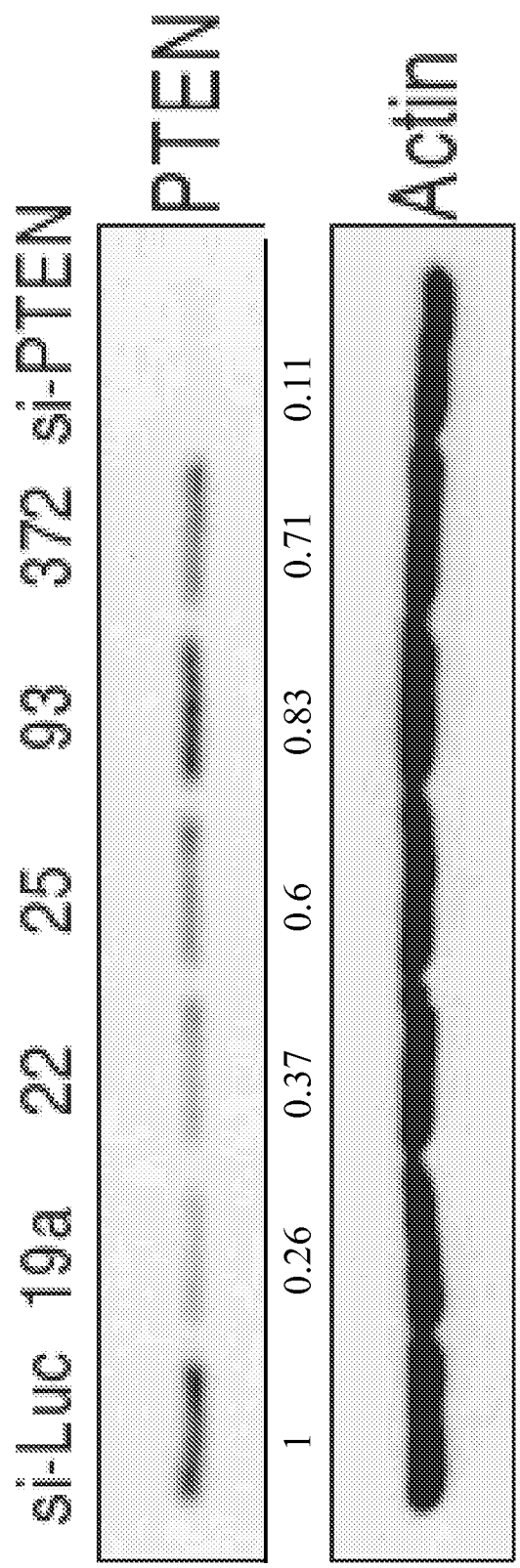
FIG. 1A-FIG. 1F show the reduction of PTEN expression levels upon cellular exposure to the indicated miRNAs.

The present invention is based, in part, on the discovery that a variety of previously unstudied oncogenic miRNAs regulate tumor suppressor genes, including PTEN and/or p53 and/or INPP4B and that these regulators can be inhibited by administration of nucleic acids that bind to them. For instance, inhibition of miRNA-based regulation of tumor suppressors can occur via chemically modified oligonucleotides, including, but not limited to LNA. Therefore, the present invention provides a platform to devise improved treatments for cancers.

In some embodiments, the present invention treats or prevents cancer in a subject through the inhibition of an miRNA. MiRNAs are short nucleic acid molecules that are able to regulate the expression of target genes. See review by Carrington et al. *Science*, Vol. 301(5631):336-338, 2003. MiRNAs are often between about 18 to 24 nucleotides in length. MiRNAs act as repressors of target mRNAs by promoting their degradation, when their sequences are perfectly complementary, and/or by inhibiting translation, when their sequences contain mismatches.

Without being bound by theory, mature miRNAs are believed to be generated by pol II or pol III and arise from initial transcripts termed -miRNAs. These pri-miRNAs are frequently several thousand bases long and are therefore processed to make much shorter mature miRNAs. These pri-miRNAs may be multicistronic and result from the transcription of several clustered sequences that organize what may develop into many miRNAs. The processing to yield miRNAs may be two-steps. First, pri-miRNAs may be processed in the nucleus by the RNase Drosha into about 70- to about 100-nucleotide hairpin-shaped precursors (pre-miRNAs). Second, after transposition to the cytoplasm, the hairpin pre-miRNAs may be further processed by the RNase Dicer to produce a double-stranded miRNA. The mature miRNA strand may then be incorporated into the RNA-induced silencing complex (RISC), where it may associate with its target mRNAs by base-pair complementarity and lead to suppression of protein expression. The other strand of the miRNA duplex that is not preferentially selected for entry into a RISC silencing complex is known as the passenger strand or minor miRNA or star (*) strand. This strand may be degraded. It is understood that, unless specified, as used herein an miRNA may refer to pri- and/or pre- and/or mature and/or minor (star) strand and/or duplex version of miRNA.

In some embodiments, miRNA genes may be located within introns of protein-coding genes or within introns or exons of noncoding transcriptional units. The expression of intronic miRNAs may coincide with that of the hosting transcriptional units because they are typically oriented in the same direction and are coordinately expressed with the pre-mRNAs in which they reside.

In some embodiments, miRNAs may bind to sequences within the 3' untranslated region (3'UTR) of target gene transcripts. In some embodiments, miRNAs may bind to sequences outside of the 3'UTR of target gene transcripts. In some embodiments, miRNAs may bind to both within and outside the 3'UTR of target gene transcripts.

Non-limiting exemplary miRNAs that bind outside the 3'UTR include miR-9 (SEQ ID NO: 1), miR-23a (SEQ ID NO: 13), miR-330-5p (SEQ ID NO: 37), miR-518c* (SEQ ID NO: 46), miR-550a (SEQ ID NO: 57), miR-659 (SEQ ID NO: 59), miR-663 (SEQ ID NO: 60), miR-671-5p (SEQ ID NO: 61), miR-760 (SEQ ID NO: 62), miR-877 (SEQ ID NO: 63), miR-1225-5p (SEQ ID NO: 64), miR-1299 (SEQ ID NO: 65), and miR-1913 (SEQ ID NO: 66).

In some embodiments, nucleotide pairing between the second and seventh nucleotides of the miRNA (the miRNA seed sequence) and the corresponding sequence along the target 3'UTR (seed match) may occur for target recognition. Accordingly, the binding between miRNA and target may comprise about a 5 nucleotide base pairing. Additionally, the binding between miRNA and target may comprise more than a 5 nucleotide base pairing.

In some embodiments, the binding between an miRNA and the gene that it regulates may be mediated by the miRNA binding up to 2, up to 4, up to 6, up to 8, or up to 10 sites of the target nucleic acid.

MiRNAs of the present invention may regulate nucleic acids, including but not limited to cancer-critical genes such as tumor suppressors, by direct binding. This binding may be perfectly complementary to the target nucleic acid or contain mismatches. The effect of this binding may be to promote degradation and/or to inhibit translation of the target.

In some embodiments, the present invention treats or prevents cancer in a subject through the inhibition of miR-NAs. In some embodiments, the miRNAs target cancer critical genes such as tumor suppressors. Non-limiting examples of tumor suppressors include PTEN, p53, and INPP4B.

In some embodiments, the inhibited cancer critical gene is the tumor suppressor PTEN. The tumor suppressor gene PTEN encodes a phosphoinositide phosphatase that opposes the phosphatidylinositol 3-kinase (PI3K)—Akt pathway. After stimulation of cells with growth factors, PI3K catalyzes the conversion of phosphatidylinositol 4,5-bisphosphate ($PIP_2$) into the second messenger phosphatidylinositol 3,4,5-trisphosphate ($PIP_3$), which then recruits various proteins that contain a pleckstrin homology (PH) domain to the plasma membrane. Among these recruited proteins is the serine and threonine kinase Akt, which is activated through phosphorylation. In turn, active Akt phosphorylates various target proteins to promote nutrient uptake, protein synthesis, cell survival, cell proliferation, cell motility, and angiogenesis. PTEN dephosphorylates $PIP_3$ to $PIP_2$, inhibiting Akt activation and thereby the PI3K-Akt signaling pathway.

Monoallelic loss or mutation of PTEN may be detected in the early stages of many sporadic tumors, including prostate cancer. High degrees of Akt phosphorylation and hyperactivation of the Akt signaling pathway are hallmarks of tumors in which PTEN function is impaired. Small decreases in PTEN protein have marked consequences on tumor initiation and progression. Accordingly, modulators of PTEN gene expression, such as the miRNAs disclosed herein, are crucial for the treatment or prevention of cancer.

Non-limiting exemplary miRNAs that may regulate PTEN may include miR-9 (SEQ ID NO: 1), miR-15b (SEQ ID NO: 2), miR-93 (SEQ ID NO: 3), miR-106a (SEQ ID NO: 4), miR-106b (SEQ ID NO: 5), miR-17-5p (SEQ ID NO: 6), miR-20a (SEQ ID NO: 7), miR-20b (SEQ ID NO: 8), miR-19a (SEQ ID NO: 9), miR-19b (SEQ ID NO: 10), miR-21 (SEQ ID NO: 11), miR-22 (SEQ ID NO: 12), miR-23a (SEQ ID NO: 13), miR-23b (SEQ ID NO: 14), miR-25 (SEQ ID NO: 15), miR-92a (SEQ ID NO: 16), miR-92b (SEQ ID NO: 17), miR-26a (SEQ ID NO: 18), miR-32 (SEQ ID NO: 19), miR-136 (SEQ ID NO: 20), miR-141 (SEQ ID NO: 21), miR-144 (SEQ ID NO: 22), miR-182 (SEQ ID NO: 23), miR-193b (SEQ ID NO: 24), miR-205 (SEQ ID NO: 25), miR-214 (SEQ ID NO: 26), miR-216a (SEQ ID NO: 27), miR-217 (SEQ ID NO: 28), miR-221 (SEQ ID NO: 29), miR-222 (SEQ ID NO: 30), miR-302a (SEQ ID NO: 31), miR-302b (SEQ ID NO: 32), miR-302c (SEQ ID NO: 33), miR-302d (SEQ ID NO: 34), miR-302e (SEQ ID NO: 35), miR-302f (SEQ ID NO: 36), miR-330-5p (SEQ ID NO: 37), miR-363 (SEQ ID NO: 38), miR-367 (SEQ ID NO: 39), miR-372 (SEQ ID NO: 40), miR-373 (SEQ ID NO: 41), miR-375 (SEQ ID NO: 42), miR-486 (SEQ ID NO: 43), miR-494 (SEQ ID NO: 44), miR-512-3p (SEQ ID NO: 45), miR-518c* (SEQ ID NO: 46), miR-518e (SEQ ID NO: 47), miR-519a (SEQ ID NO: 48), miR-519b-3p (SEQ ID NO: 49), miR-519c (SEQ ID NO: 50), miR-519d (SEQ ID NO: 51), miR-520a (SEQ ID NO: 52), miR-520b (SEQ ID NO: 53), miR-520c (SEQ ID NO: 54), miR-520d (SEQ ID NO: 55), miR-520e (SEQ ID NO: 56), miR-550a (SEQ ID NO: 57), miR-625 (SEQ ID NO: 58), miR-659 (SEQ ID NO: 59), miR-663 (SEQ ID NO: 60), miR-671-5p (SEQ ID NO: 61), miR-760 (SEQ ID NO: 62), miR-877 (SEQ ID NO: 63), miR-1225-5p (SEQ ID NO: 64), miR-1299 (SEQ ID NO: 65), miR-1913 (SEQ ID NO: 66) and miR-23* (SEQ ID NO:67).

In some embodiments, the inhibited cancer critical gene is the tumor suppressor p53. The nuclear phosphoprotein p53 is a tumor suppressor protein that is ubiquitously expressed at low levels in normal tissues, including thymus, spleen and lymphohematopoetic cells. Inactivation or loss of p53 is a common event associated with the development of human cancers. Functional inactivation may occur as a consequence of genetic aberrations within the p53 gene, including missense mutations, or interaction with vital and cellular oncogenes. Loss of wild-type (wt) p53 functions may lead to uncontrolled cell cycling and replication, inefficient DNA repair, selective growth advantage and, consequently, tumor formation, among other effects. Accordingly, p53 is thought of as a "master watchman" of the genome, referring to its role in conserving stability by preventing genome mutations. Accordingly, reduction of p53, for instance by miRNAs, may induce cancer as the protective effects of this gene would be lost.

Non-limiting exemplary miRNAs that may regulate p53 may include miR-9 (SEQ ID NO: 1), miR-106a (SEQ ID NO: 4), miR-17-5p (SEQ ID NO: 6), miR-20a (SEQ ID NO: 7), miR-20b (SEQ ID NO: 8), miR-19b (SEQ ID NO: 10), miR-23a (SEQ ID NO: 13), miR-26a (SEQ ID NO: 18), miR-205 (SEQ ID NO: 25), miR-216a (SEQ ID NO: 27), miR-302c (SEQ ID NO: 33), miR-302d (SEQ ID NO: 34), miR-302e (SEQ ID NO: 35, miR-330-5p (SEQ ID NO: 37), miR-375 (SEQ ID NO: 42), 512-3p (SEQ ID NO: 45), miR-518c* (SEQ ID NO: 46), miR-519a (SEQ ID NO: 48), miR-625 (SEQ ID NO: 58), miR-659 (SEQ ID NO: 59), miR-663 (SEQ ID NO: 60), miR-671-5p (SEQ ID NO: 61), miR-760 (SEQ ID NO: 62), miR-1225-5p (SEQ ID NO: 64), miR-1299 (SEQ ID NO: 65), miR-1913 (SEQ ID NO: 66) and miR-23* (SEQ ID NO:67).

In some embodiments, the inhibited cancer critical gene is the tumor suppressor INPP4B. INPP4B is an enzyme that hydrolyzes the 4-position phosphate of $PI(3,4)P_2$, and to a lesser degree inositol(3,4)bisphosphate ($Ins(3,4)P_2$) and $Ins(3,4,5)P_3$, in vitro. In vivo, it is believed to play a role in the PI3K-Akt signaling pathway. In this system, two major phospholipid pools are generated: $PI(3,4,5)P_3$ and $PI(3,4)P_2$. PTEN, described above, hydrolyzes the 3'-phosphate of $PI(3,4,5)P_3$ to terminate PI3K signaling. However, src-homology 2-containing inositol 5' phosphatase (SHIP) family members hydrolyze the 5'-phosphate of $PI(3,4,5)P_3$ to generate $PI(3,4)P_2$, which, like $PI(3,4,5)P_3$, can facilitate PDK1-dependent phosphorylation and activation of AKT, which, as described above, is a serine/threonine protein kinase that has been linked to cancer. INPP4B converts $PI(3,4)P_2$ to $PI(3)P$. Loss of PTEN or loss of INPP4B results in prolonged activation of Akt, and subsequently in increased cell proliferation, cell migration, and invasion.

Non-limiting exemplary miRNAs that may regulate INPP4B may include miR-15b (SEQ ID NO: 2), miR-93 (SEQ ID NO: 3), miR-21 (SEQ ID NO: 11), miR-22 (SEQ ID NO: 12), miR-92a (SEQ ID NO: 16), miR-92b (SEQ ID NO: 17), miR-32 (SEQ ID NO: 19), miR-182 (SEQ ID NO: 23), miR-205 (SEQ ID NO: 25), miR-221 (SEQ ID NO: 29), miR-302a (SEQ ID NO: 31), miR-302b (SEQ ID NO: 32), miR-302c (SEQ ID NO: 33), miR-302d (SEQ ID NO: 34), miR-330-5p (SEQ ID NO: 37), miR-363 (SEQ ID NO: 38), miR-367 (SEQ ID NO: 39), miR-372 (SEQ ID NO: 40), miR-373 (SEQ ID NO: 41), miR-375 (SEQ ID NO: 42), miR-486 (SEQ ID NO: 43), miR-512-3p (SEQ ID NO: 45), miR-518c* (SEQ ID NO: 46), miR-519a (SEQ ID NO: 48), miR-519b-3p (SEQ ID NO: 49), miR-520b (SEQ ID NO: 53), miR-520e (SEQ ID NO: 56), miR-550a (SEQ ID NO: 57), miR-625 (SEQ ID NO: 58), miR-659 (SEQ ID NO: 59), miR-663 (SEQ ID NO: 60), miR-671-5p (SEQ ID NO: 61), miR-760 (SEQ ID NO: 62), miR-877 (SEQ ID NO: 63), miR-1225-5p (SEQ ID NO: 64), and miR-1299 (SEQ ID NO: 65).

In some embodiments, the sequence of the inhibitor is taken, in part, from the sequence of a human transcript. In some embodiments, the inhibitor of miRNA is selected based on the tissue environment of the cancer. In some embodiments, the inhibitor is selected to reduce the expression and/or activity of the target miRNA in a subject.

In some embodiments, an inhibitor of miRNA is an antisense oligonucleotide. Antisense oligonucleotides can include ribonucleotides or deoxyribonucleotides or a combination thereof. Antisense oligonucleotides may have at least one chemical modification (non-limiting examples are sugar or backbone modifications). For instance, suitable antisense oligonucleotides can be comprised of one or more conformationally constrained or bicyclic sugar nucleoside modifications (BSN) that confer enhanced thermal stability to complexes formed between the oligonucleotide containing BSN and their complementary miRNA target strand. For example, in one embodiment, the antisense oligonucleotides contain at least one locked nucleic acid. Locked nucleic acids (LNAs) contain a 2'-O, 4'-C-methylene ribonucleoside (structure A) wherein the ribose sugar moiety is in a locked conformation. In another embodiment, the antisense oligonucleotides contain at least one 2', 4'-C-bridged 2' deoxyribonucleoside (CDNA, structure B). See, e.g., U.S. Pat. No. 6,403,566 and Wang et al. (1999) *Bioorganic and Medicinal Chemistry Letters*, Vol. 9: 1147-1150, both of which are herein incorporated by reference in their entireties. In yet another embodiment, the antisense oligonucleotides contain at least one modified nucleoside having the structure shown in structure C. The antisense oligonucleotides targeting miRNAs that regulate tumor suppressors can contain combinations of BSN (LNA, CDNA, and the like) or other modified nucleotides, and ribonucleotides or deoxyribonucleotides.

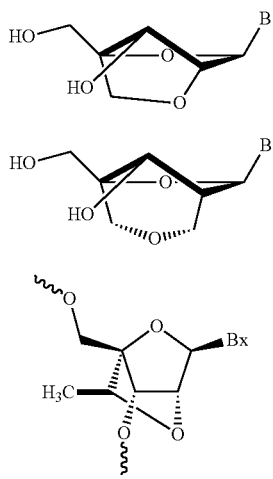

Alternatively, the antisense oligonucleotides can comprise peptide nucleic acids (PNAs), which contain a peptide-based backbone rather than a sugar-phosphate backbone. Other modified sugar or phosphodiester modifications to the antisense oligonucleotide are also contemplated. By way of non-limiting examples, other chemical modifications can include 2'-O-alkyl (e.g., 2'-O-methyl, 2'-O-methoxyethyl), 2'-fluoro, and 4'-thio modifications, and backbone modifications, such as one or more phosphorothioate, morpholino, or phosphonocarboxylate linkages (see, e.g., U.S. Pat. Nos. 6,693,187 and 7,067,641, which are herein incorporated by reference in their entireties). In one embodiment, antisense oligonucleotides targeting oncogenic miRNAs contain 2'-O-methyl sugar modifications on each base and are linked by phosphorothioate linkages. Antisense oligonucleotides, particularly those of shorter lengths (e.g., less than 16 nucleotides, 7-8 nucleotides) can comprise one or more affinity enhancing modifications, such as, but not limited to, LNAs, bicyclic nucleosides, phosphonoformates, 2' O-alkyl modifications, and the like. In some embodiments, suitable antisense oligonucleotides are 2'-O-methoxyethyl gapmers which contain 2'-O-methoxyethyl-modified ribonucleotides on both 5' and 3' ends with at least ten deoxyribonucleotides in the center. These gapmers are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. For instance, and not intending to be limiting, to facilitate in vivo delivery and stability, the antisense oligonucleotide can be linked to a steroid, such as cholesterol moiety, a vitamin, a fatty acid, a carbohydrate or glycoside, a peptide, or other small molecule ligand at its 3' end.

In some embodiments, antisense oligonucleotides useful for inhibiting the activity of miRNAs are about 5 to about 25 nucleotides in length, about 10 to about 30 nucleotides in length, or about 20 to about 25 nucleotides in length. In certain embodiments, antisense oligonucleotides targeting oncogenic miRNAs are about 8 to about 18 nucleotides in length, in other embodiments about 12 to about 16 nucleotides in length, and in other embodiments about 7-8 nucleotides in length. Any 7-mer or longer complementary to an oncogenic miRNA may be used, i.e., any anti-miR complementary to the 5' end of the miRNA and progressing across the full complementary sequence of the miRNA.

Antisense oligonucleotides can comprise a sequence that is at least partially complementary to a mature or minor (i.e. star) oncogenic miRNA sequence, e.g., at least about 75%, 80%, 85%, 90%, 95%, 96%, 97%, 98%, or 99% complementary to a mature or minor (i.e. star) oncogenic miRNA sequence. In some embodiments, the antisense oligonucleotide can be substantially complementary to a mature or minor oncogenic miRNA sequence, that is at least about 90%, 95%, 96%, 97%, 98%, or 99% complementary to a target polynucleotide sequence. In one embodiment, the antisense oligonucleotide comprises a sequence that is 100% complementary to a mature or minor oncogenic miRNA sequence.

As used herein, substantially complementary refers to a sequence that is at least about 95%, 96%, 97%, 98%, 99%, or 100% complementary to a target polynucleotide sequence (non-limiting examples are mature, minor, precursor miRNA, or pri-miRNA sequence).

In some embodiments, the antisense oligonucleotides are antagomirs. Antagomirs are single-stranded, chemically-modified ribonucleotides that are at least partially complementary to miRNAs and therefore may silence them. See, e.g., Krützfeldt, et al. *Nature* (2005) 438 (7068): 685-9. Antagomirs may comprise one or more modified nucleotides, such as 2'-O-methyl-sugar modifications. In some embodiments, antagomirs comprise only modified nucleotides. Antagomirs can also comprise one or more phosphorothioate linkages resulting in a partial or full phosphorothioate backbone. To facilitate in vivo delivery and stability, the antagomir can be linked to a cholesterol or other moiety at its 3' end. Antagomirs suitable for inhibiting can be about 15 to about 50 nucleotides in length, about 18 to about 30 nucleotides in length, and about 20 to about 25 nucleotides in length. The antagomirs can be at least about 75%, 80%, 85%, 90%, 95%, 96%, 97%, 98%, or 99% complementary to a mature or minor oncogenic miRNA sequence. In some embodiments, the antagomir may be substantially complementary to a mature or minor oncogenic miRNA sequence, that is at least about 95%, 96%, 97%, 98%, or 99% complementary to a target polynucleotide sequence. In other embodiments, the antagomirs are 100% complementary to a mature or minor oncogenic miRNA sequence.

Antisense oligonucleotides or antagomirs may comprise a sequence that is substantially complementary to a precursor miRNA sequence (pre-miRNA) or primary miRNA sequence (pri-miRNA) of an oncogenic miRNA. In some embodiments, the antisense oligonucleotide comprises a sequence that is located outside the 3'-untranslated region of a target of that miRNA. In some embodiments, the antisense oligonucleotide comprises a sequence that is located inside the 3'-untranslated region of a target of that miRNA.

Any of the inhibitors or agonists of the oncogenic miRNAs described herein can be delivered to a target cell (a non-limiting example is a cancer cell) by delivering to the cell an expression vector encoding the miRNA inhibitors or agonists. A vector is a composition of matter which can be used to deliver a nucleic acid of interest to the interior of a cell. Numerous vectors are known in the art, including, but not limited to, linear polynucleotides, polynucleotides associated with ionic or amphiphilic compounds, plasmids, and viruses. Thus, the term vector includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms expression construct, expression vector, and vector are used interchangeably to demonstrate the application of the invention in a general, illustrative sense, and are not intended to limit the invention.

In one embodiment, an expression vector for expressing an inhibitor of an oncogenic miRNA comprises a promoter operably linked to a polynucleotide encoding an antisense oligonucleotide. The sequence of the expressed antisense oligonucleotide may be partially or perfectly complementary to a mature or minor sequence of an oncogenic miRNA. The phrase operably linked or under transcriptional control as used herein means that the promoter is in the correct location and orientation in relation to a polynucleotide to control the initiation of transcription by RNA polymerase and expression of the polynucleotide.

As used herein, a promoter refers to a DNA sequence recognized by the synthetic machinery of the cell, or introduced synthetic machinery, required to initiate the specific transcription of a gene. Suitable promoters include, but are not limited to, RNA pol I, pol II, pol III, and viral promoters (e.g., human cytomegalovirus (CMV) immediate early gene promoter, the SV40 early promoter, and the Rous sarcoma virus long terminal repeat). In one embodiment, the promoter is a tissue-specific promoter, such as, by way of non-limiting example, the prostate-specific Probasin promoter $ARR_2PB$.

In certain embodiments, the promoter operably linked to a polynucleotide encoding an miRNA inhibitor or a polynucleotide encoding a tumor-suppressor regulating miRNA can be an inducible promoter. Inducible promoters are known in the art and include, but are not limited to, the tetracycline promoter, the metallothionein IIA promoter, the heat shock promoter, the steroid/thyroid hormone/retinoic acid response elements, the adenovirus late promoter, and the inducible mouse mammary tumor virus LTR.

Methods of delivering expression constructs and nucleic acids to cells are known in the art and can include, by way of non-limiting example, calcium phosphate co-precipitation, electroporation, microinjection, DEAE-dextran, lipofection, transfection employing polyamine transfection reagents, cell sonication, gene bombardment using high velocity microprojectiles, and receptor-mediated transfection.

The present invention also includes scavenging or clearing inhibitors of oncogenic miRNAs following treatment. Scavengers may include isolated nucleic acids that are complementary to miRNA inhibitors or vectors expressing the same. Therefore, they may bind to miRNA inhibitors or vectors expressing the same and, in doing so, prevent the binding between miRNA and target. The method may comprise overexpressing binding sites for the tumor suppressive inhibitors in a tissue.

Another embodiment of the present invention is a method of treating or preventing cancer in a subject. Cancer is a group of diseases characterized by uncontrolled cell division which can lead to abnormal tissue and, in turn, disruption of normal physiologic processes and, possibly, death. Cancer cells may be able to grow in the absence of the growth promoting factors required for the proliferation of normal cells. Further, cancer cells may be resistant to normal signals that control apoptosis.

Cancer cells may form a tumor. Cancer cells may also be leukemias. Tumors may be benign and therefore lack the invasive effects of cancer. Tumors may also be pre-malignant; that is, the tumor may lead to cancer if left untreated. Malignant tumors may be characterized by a tendency to become progressively worse and to potentially result in death. Malignant tumors may be characterized by anaplasia, invasiveness, and metastasis. Malignancy is often a touchstone of cancer.

Cancers may be localized, which includes cancers that reside in a single tissue environment. Cancers may also be metastatic. In this case, cancer cells may invade surrounding tissues, frequently by breaking through the basal laminas that create tissue boundaries, and spread to other areas of the body where they may establish secondary areas of growth.

Cancer causation may be linked to genetic and environmental factors. Exemplary cancer-critical genes can be classified roughly into two groups based on whether mutations in them cause loss of function or gain of function outcomes. Loss-of-function mutations of tumor suppressor genes relieve cells of inhibitions that normally help to hold their numbers in check, while gain-of-function mutations of proto-oncogenes stimulate cells to increase their numbers when they should not. Notable tumor suppressor genes include PTEN, p53, and INPP4B, among many others.

In some embodiments, the present invention encompasses methods of treating or preventing cancer in a subject in need thereof. In some embodiments, the cancer is selected from a group consisting of: brain, kidney, liver, adrenal gland, bladder, cervix, breast, stomach, ovaries, esophagus, neck, head, eye, skin, colon, rectum, prostate, pancreas, liver, lung, vagina, thyroid, gastrointestinal, blood, glioblastoma, sarcoma, multiple myeloma, melanoma, metastasis of primary tumor sites, myeloproliferative disease, leukemia, papillary thyroid carcinoma, non small cell lung cancer, mesothelioma, and gastrointestinal stromal tumor. See, e.g., Weinberg, *The Biology of Cancer*, Garland Science: London 2006, the contents of which are hereby incorporated by reference.

In some embodiments, the cancer to be treated or prevented is prostate cancer. Prostate cancer afflicts one out of nine men over age 65 and is a leading cause of male cancer-related death. See Abate-Shen and Shen, 2000, *Genes Dev.* 14:2410; Ruijter et al., 1999, *Endocr Rev,* 20:22). Prostate cancer is typically diagnosed with a digital rectal exam and/or prostate specific antigen (PSA) screening. In the latter, an elevated serum PSA level can indicate the presence of prostate cancer. PSA is used as a marker for prostate cancer because it is secreted only by prostate cells. A healthy prostate will produce a stable amount of PSA, typically below 4 nanograms per milliliter, or a PSA reading of 4 or less, whereas cancer cells produce escalating amounts that correspond with the severity of the cancer. PSA levels of about 4-10 suggest a possibility of prostate cancer in a subject while a PSA level above 50 may be indicative of a tumor that has spread elsewhere in the body.

Biopsies of various sectors of the prostate are used to determine if prostate cancer is present. Current treatment options depend on the stage of the cancer. Biopsied tissues may be scored by a pathologist when undertaking microscopic evaluation of a biopsied sample. A Gleason score may be assigned to a tissue based on architectural features of the tumor. The Gleason scoring system identifies five different patterns of cancer, i.e., assigns a number from 1 to 5, based on how close to normal (differentiated) the cancer looks under a microscope. A Gleason score of 1 is the most differentiated (or benign appearing) pattern while a Gleason score of 5 is the most de-differentiated (or aggressive appearing) pattern. Two common patterns of differentiation are evaluated to generate two scores of 1-5 which are summed to yield a tumor's Gleason score (which can range from 2-10). Many prostate cancer cases have Gleason grades of 5, 6, or 7 while more aggressive forms of prostate cancer have scores of 8, 9, or 10.

Men with a lower life expectancy, a low Gleason number, and whose tumor is localized to the prostate are often not treated but subject to monitoring or watchful waiting. More aggressive cancers may be treated with the following non-limiting examples. For instance, surgical treatments such as radical prostatectomy (RP), in which the prostate is completely removed (with or without nerve sparing techniques) and radiation, which may be applied through an external beam that directs the dose to the prostate from outside the body or via low-dose radioactive seeds that are implanted within the prostate to kill cancer cells locally may be used. Combination therapies are also possible. Hormone therapy may also be used, alone or in conjunction with surgery or radiation or other treatments. As a non-limiting example, anti-androgen hormone therapy may use luteinizing hormone-releasing hormones (LH-RH) analogs, which block the pituitary from producing hormones that stimulate testosterone production. While surgical and hormonal treatments are often effective for localized prostate cancer, treatment of advanced disease is currently less successful. Androgen ablation is the most common therapy for advanced prostate cancer, leading to massive apoptosis of androgen-dependent malignant cells and temporary tumor regression.

The present invention, in some embodiments, may be used to treat localized or metastatic prostate cancers.

Also, the present invention, in part, provides an additional treatment or prevention method for subjects afflicted with cancer. As used herein, the term subject or patient refers to any vertebrate including, without limitation, humans and other primates (e.g., chimpanzees and other apes and monkey species), farm animals (e.g., cattle, sheep, pigs, goats, and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal.

Another embodiment of the present invention is a pharmaceutical composition comprising an inhibitor of an miRNA that regulates PTEN and/or p53 and/or INPP4B and a pharmaceutically acceptable carrier. This may include administration of one or more inhibitors of oncogenic miRNAs. Where clinical applications are contemplated, pharmaceutical compositions may be prepared in a form appropriate for the intended application. Generally, this will entail preparing compositions that are essentially free of pyrogens, as well as other impurities that could be harmful to humans or animals.

In one embodiment, a pharmaceutical composition comprises an effective dose of an miRNA inhibitor and a pharmaceutically acceptable carrier. An effective dose is an amount sufficient to effect a beneficial or desired clinical result. An effective dose of an miRNA inhibitor of the invention may be from about 1 mg/kg to about 100 mg/kg, about 2.5 mg/kg to about 50 mg/kg, or about 5 mg/kg to about 25 mg/kg. The precise determination of what would be considered an effective dose may be based on factors individual to each patient, including their size, age, type of cancer, and nature of inhibitor or agonist (non-limiting examples include antagomir, expression construct, antisense oligonucleotide, polynucleotide duplex, etc.). Therefore, dosages can be readily ascertained by those of ordinary skill in the art from this disclosure and the knowledge in the art.

A beneficial or desired clinical result may include, inter alia, a reduction in tumor size and/or tumor growth and/or a reduction of a cancer marker that is associated with the presence of cancer as compared to what is observed without administration of the inhibitor. In the treatment of prostate cancer, for example, a beneficial or desired clinical result may include, inter alia, a reduction in a prostate specific antigen score as compared to what is observed without administration of the inhibitor. A beneficial or desired clinical result may also include, inter alia, an increased presence of a marker that is associated with a reduction of cancer as compared to what is observed without administration of the inhibitor. Also included in a beneficial or desired clinical result is, inter alia, an increased amount of tumor suppressor mRNA or protein as compared to what is observed without administration of the inhibitor. The increased tumor suppressor may include, for example, PTEN and/or p53 and/or INPP4B.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the oligonucleotide inhibitors of oncogenic miRNA function, polynucleotides encoding tumor suppressor miRNA agonists, or constructs expressing particular miRNA inhibitors or agonists. Commercially available fat emulsions that are suitable for delivering the nucleic acids of the invention to cancer tissues include Intralipid®, Liposyn®, Liposyn® II, Liposyn® III, Nutrilipid, and other similar lipid emulsions. A colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449, which are herein incorporated by reference in their entireties.

One will generally desire to employ appropriate salts and buffers to render delivery vehicles stable and allow for uptake by target cells. Aqueous compositions of the present invention comprise an effective amount of the delivery vehicle comprising the inhibitor polynucleotides (e.g., liposomes or other complexes or expression vectors) dissolved or dispersed in a pharmaceutically acceptable carrier or aqueous medium. The phrases pharmaceutically acceptable or pharmacologically acceptable refer to molecular entities and compositions that do not produce adverse, allergic, or other untoward reactions when administered to an animal or a human. As used herein, pharmaceutically acceptable carrier includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or polynucleotides of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cancer tissue. The agents disclosed herein may also be administered by catheter systems. Such compositions would normally be administered as pharmaceutically acceptable compositions as described herein.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions may be administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic with, for example, sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion (see, e.g, *Remington's Pharmaceutical Sciences*, 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by the FDA Office of Biologics standards.

In another embodiment of the present invention includes a method of treating or preventing cancer in a subject in need thereof comprising administering to the subject: a first inhibitor of a first miRNA, wherein the miRNA is a PTEN regulator and a second inhibitor of a second miRNA, wherein the miRNA is a p53 regulator or an INPP4B regulator, wherein said first and second inhibitors may be administered in either order or concurrently.

In another embodiment of the present invention includes a method of treating or preventing cancer in a subject in need thereof comprising administering to the subject a first agent that is or comprises an inhibitor of at least one miRNA, wherein the miRNA is a PTEN regulator and a second agent that is or comprises at least one other cancer biologic, therapeutic, chemotherapeutic or drug, wherein said second agent acts at a non-PTEN target or pathway in cells of said cancer, wherein said first and second agents may be administered in either order or concurrently.

In some embodiments, the present invention includes various cancer biologics, therapeutics, chemotherapeutics, or drugs known in the art. For exemplary purposes only, and not intending to be limiting, the following drugs may be used in the present invention:

| Drug Name | Alternative Nomenclature |
|---|---|
| Altretamine | Hexalen ®, hydroxymethylpentamethylmelamine (HMPMM) |
| Bleomycin | Blenoxane ® |
| Carboplatin | Paraplatin ® |
| Carmustine | BCNU, BiCNU ® |
| Cisplatin | Platinol ®, CDDP |
| Cyclophosphamide | Cytoxan ®, Neosar ®, 4-hydroperoxycyclophosphamide, 4-HC |

-continued

| Drug Name | Alternative Nomenclature |
| --- | --- |
| Docetaxel | Taxotere ®, D-Tax |
| Doxorubicin | Adriamycin ®, Rubex ®, Doxil ® |
| Epirubicin | Ellence ® |
| Erlotinib | Tarceva ®, OSI-774 |
| Etoposide | VePesid ®, Etopophos ®, VP-16 |
| Fluorouracil | Adrucil ®, 5-FU, Efudex ®, Fluoroplex ®, Capecitabine*, Xeloda ® |
| Gemcitabine | Gemzar ® |
| Ifosfamide | Ifex ®, 4-hydroperoxyifosfamide, 4-HI |
| Irinotecan/SN-38 | Camptosar ®, CPT-11, SN-38 |
| Leucovorin | Wellcovorin ® |
| Lomustine | CCNU, CeeNU ® |
| Melphalan | Alkeran ®, L-PAM |
| Mitomycin | Mutamycin ®, Mitozytrex ®, Mitomycin-C |
| Oxaliplatin | Eloxatin ® |
| Paclitaxel | Taxol ®, Abraxane ® |
| Procarbazine | Matulane ®, PCZ |
| Temozolomide | Temodar ® |
| Topotecan | Hycamtin ® |
| Vinblastine | Velban ®, Exal ®, Velbe ®, Velsar ®, VLB |
| Vincristine | Oncovin ®, Vincasar PFS ®, VCR |
| Vinorelbine | Navelbine ®, NVB |

Another embodiment of the present invention includes a method of treating or preventing cancer in a subject in need thereof comprising administering an inhibitor of an oncogenic miRNA and/or cancer biologic, therapeutic, chemotherapeutic or drug which includes the further step of diagnosing a patient to identify the regulated tumor suppressor before treatment. Such diagnosis can include, among others, actually making the evaluation of tumor suppressor regulation or ordering that such a determination be made. Further, the selection of miRNA inhibitor and/or cancer biologic, therapeutic, chemotherapeutic or drug would be educated by the diagnosis.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1: A Group of miRNAs that Regulate Tumor Suppressor Genes

Computational studies were undertaken to identify potential tumor suppressor-targeting miRNAs. Particularly, four target prediction databases were used to generate a pool of possible PTEN targeting miRNAs: TargetScanS (Lewis et al., Cell. 2005; 120:15-20), PicTar (Krek et al., Nat Genet. 2005; 37: 495-500), miRanda (John et al., PLoS Biol. 2004; 2:e363), and miRBase (Griffiths-Jones et al., Nucleic Acids Res. 2006; 34: D140-D144). This pool was focused using a two-step selection criteria that selected for miRNA families that (i) had oncogenic potential and (ii) were predicted to target PTEN by multiple algorithms (see Poliseno, et al. Sci Signal. 2010 Apr. 13; 3(117): ra29, the contents of which are hereby incorporated by reference). Many of the miRNAs that fit these criteria are listed in Table 1.

All of the miRNAs in Table 1 were validated as being able to regulate PTEN. By way of example, the ability of miR-19a, miR-22, miR-25, miR-93, and miR-372 to decrease the abundance of PTEN is shown in FIG. 1A-FIG. 1F. Each of the five miRNAs were overexpressed as a synthetic short interfering-like molecule (si-miRNA) in the DU145 prostate cancer cell line using molecular biology techniques known in the art (see Poliseno, et al. Sci Signal. 2010 Apr. 13; 3(117):ra29). This DU145 prostate cancer cell line is wild type for PTEN and the expressed 3'UTR harbors all the predicted miRNA binding sites.

The abundance of PTEN protein was reduced by all tested miRNAs. Transfected DU145 cells were grown for specified time points and were collected and lysed in 50 mM tris (pH 8.0), 1 mM EDTA, 1 mM $MgCl_2$, 1% NP-40, 1 mM β-glycerophosphate, 1 mM $Na_3VO_4$, 1 mM NaF, and various protease inhibitors. Proteins (30 µg per lane) were separated on 10% SDS-polyacrylamide gel and transferred to nitrocellulose membranes. Immunoblotting of the membranes was performed with primary antibodies against PTEN (1:1000) and actin (1:10000). Signals were revealed after incubation with the recommended secondary antibody coupled to peroxidase by enhanced chemiluminescence. Scanned images were quantified with ImageJ software. FIG. 1A shows the reduction of PTEN protein levels upon cellular transfection with the above mentioned miRNAs.

Figure 1B:
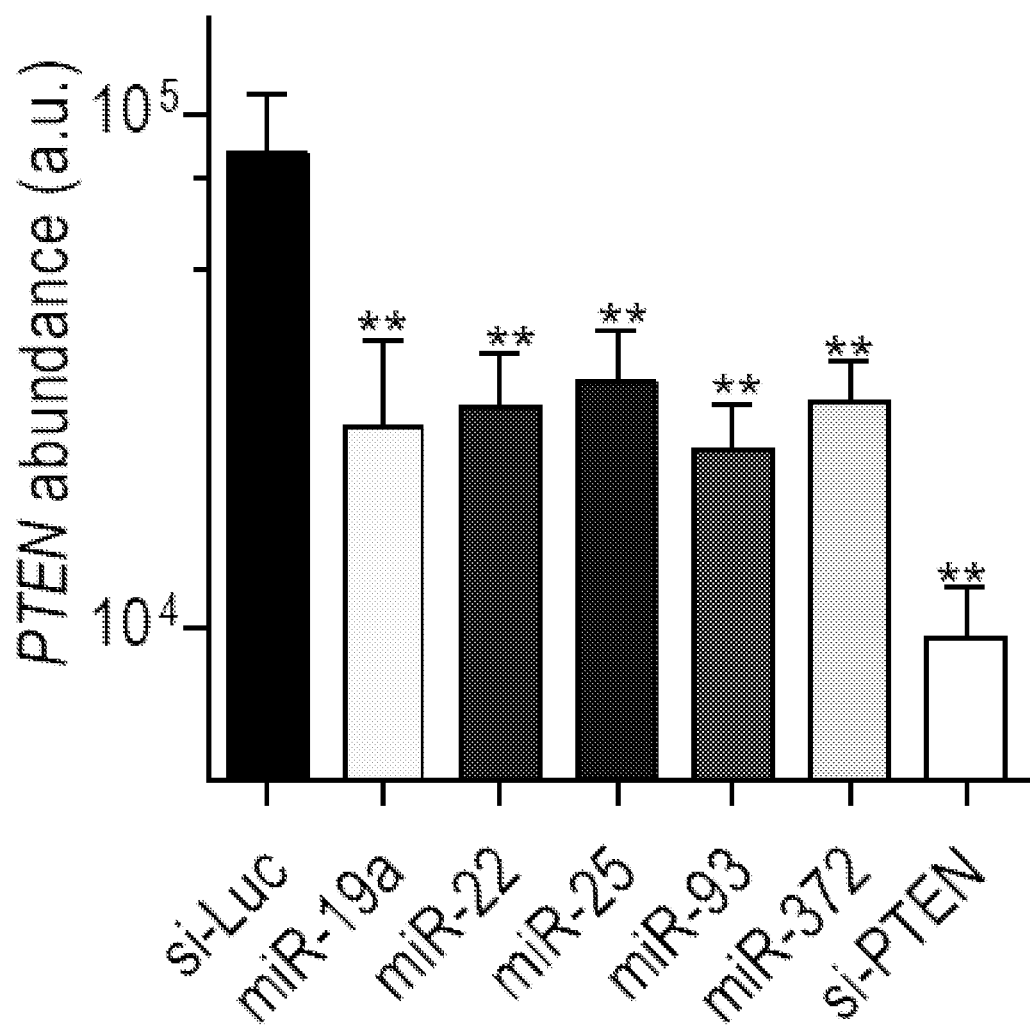

Further, the abundance of PTEN transcript was reduced by all tested miRNAs. Real time PCR, which is well known in the art, was used to make this determination. Briefly, real-time PCR was carried out with Sybr Green fluorescence. Two microliters of cDNA was used in a 20-µl reaction. Actin (human) was used as an internal standard. Relative quantification of gene expression was performed with the comparative $C_T$ method. As shown in FIG. 1B, miRNA members of the miR-17, miR-19, miR-22, miR-25, and miR-302 families mentioned above cause a decrease in the abundance of PTEN mRNA.

Figure 1C:
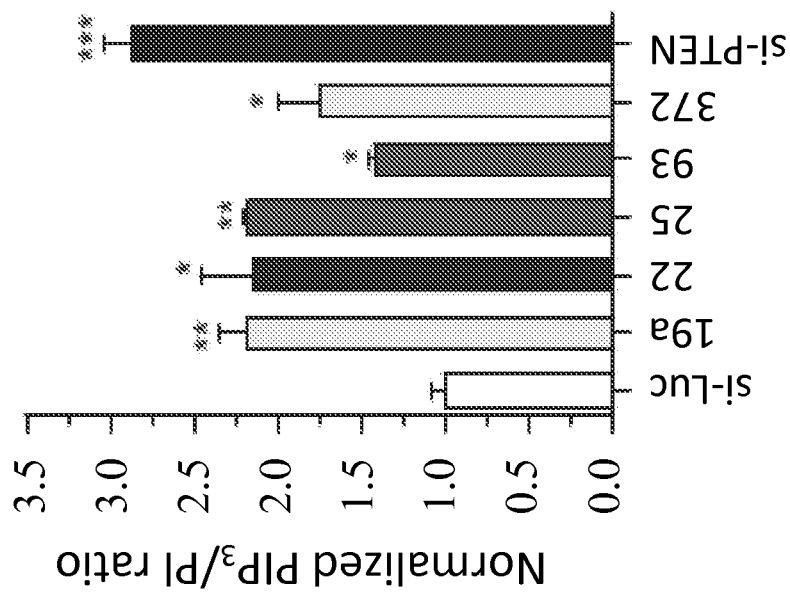
Figure 1C:
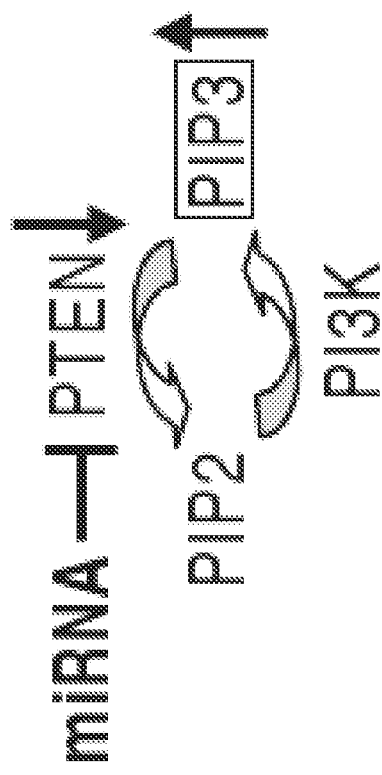

This miRNA-mediated reduction in PTEN activity was also shown functionally using phosphoinositide analysis. As described above, PTEN's substrate is PIP3. Therefore, PTEN activity can be indirectly assessed by measuring the abundance of PIP3. Briefly, DU145 cells were seeded at $3\times10^5$ cells per six-well dish. The following day, these cells were transfected with the different si-miRNAs. Six hours after transfection, cells of one six-well plate were trypsinized and replated in two 10-cm plates. The following day, the cells were labeled for 24 hours with [$^3$H]inositol (10 mCi/ml) for 24 hours in inositol-free DMEM media supplemented with 10% FBS and 0.5% BSA. The cells were then serum-starved for 24 hours in inositol-free DMEM with [$^3$H]inositol (10 mCi/ml) and 0.5% BSA, but without FBS. After 5 minutes of stimulation with 200 nM insulin, cells were lysed in 1M HCl. Lipids were extracted in chloroform-methanol (1:1, vol/vol) and deacylated as known in the art (Serunian et al., Methods Enzymol. 1991; 198: 78-87). Phosphatidylinositides were separated by anion-exchange high-performance liquid chromatography (Beckman), detected by a flow scintillation analyzer (Perkin-Elmer), and quantified with ProFSA software (Perkin-Elmer). The $^3$H-labeled PI3P (phosphatidylinositol 3-phosphate), $PIP_2$, and $PIP_3$ peaks were identified by $^{32}$P-labeled in vitro synthesized internal lipid standards, prepared with baculovirus-expressed PI3K. For the [$^3$H]inositol labeling, the counts in each peak were normalized against the counts found in the phosphatidylinositol peak. FIG. 1C shows that overexpression of PTEN-regulating miRNAs led to increased levels of PIP3, suggesting decreased activity of PTEN.

Figure 1D:
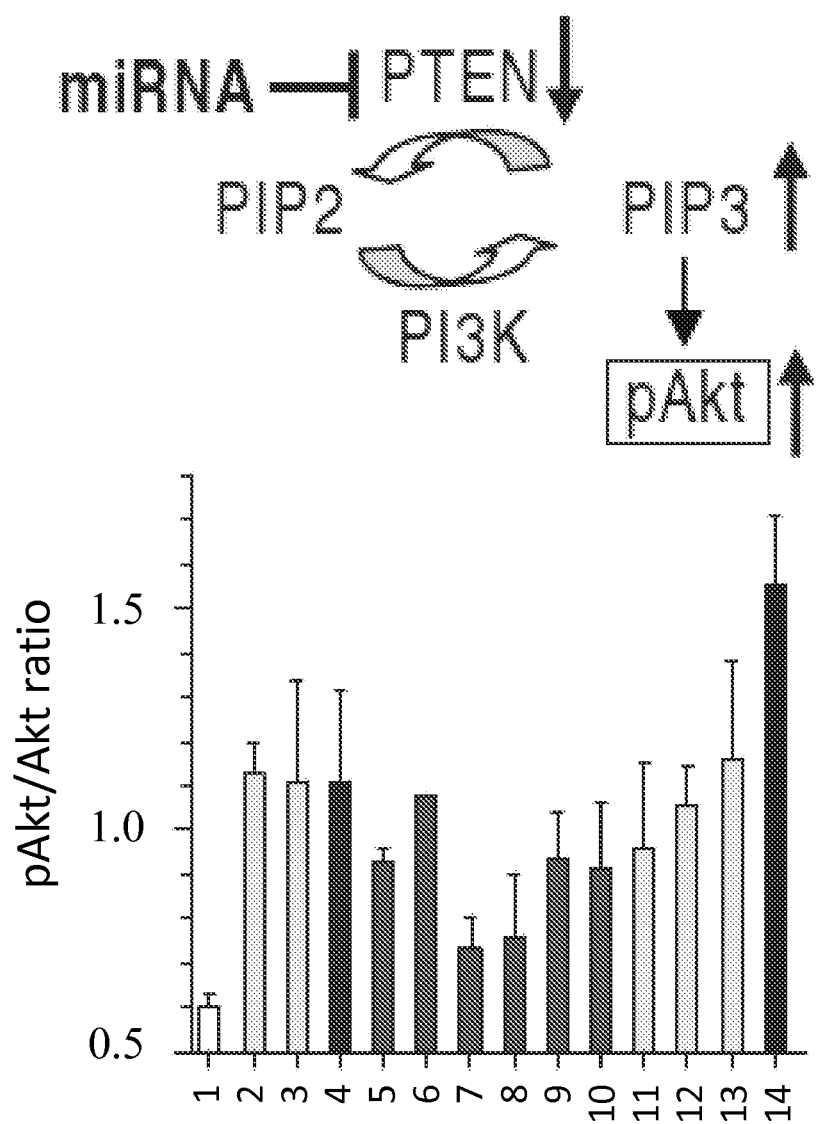

The miRNA-mediated decrease in PTEN abundance was further confirmed functionally by the observation of increased Akt phosphorylation. As described above, PTEN dephosphorylates $PIP_3$ to $PIP_2$, inhibiting Akt activation (which is mediated through its phosphorylation). FIG. 1D shows the pAkt/Akt ratio in PWR-1E cells after the transient transfection of 1: si-Luc; 2 to 13: si-miRNAs 19a, 19b (miR-19 family), 22, 25, 92a (miR-25 family), 17, 20a, 93, 106b (miR-17 family), 302a, 372, 373 (miR-302 family); and 14: siPTEN.

Figure 1E:
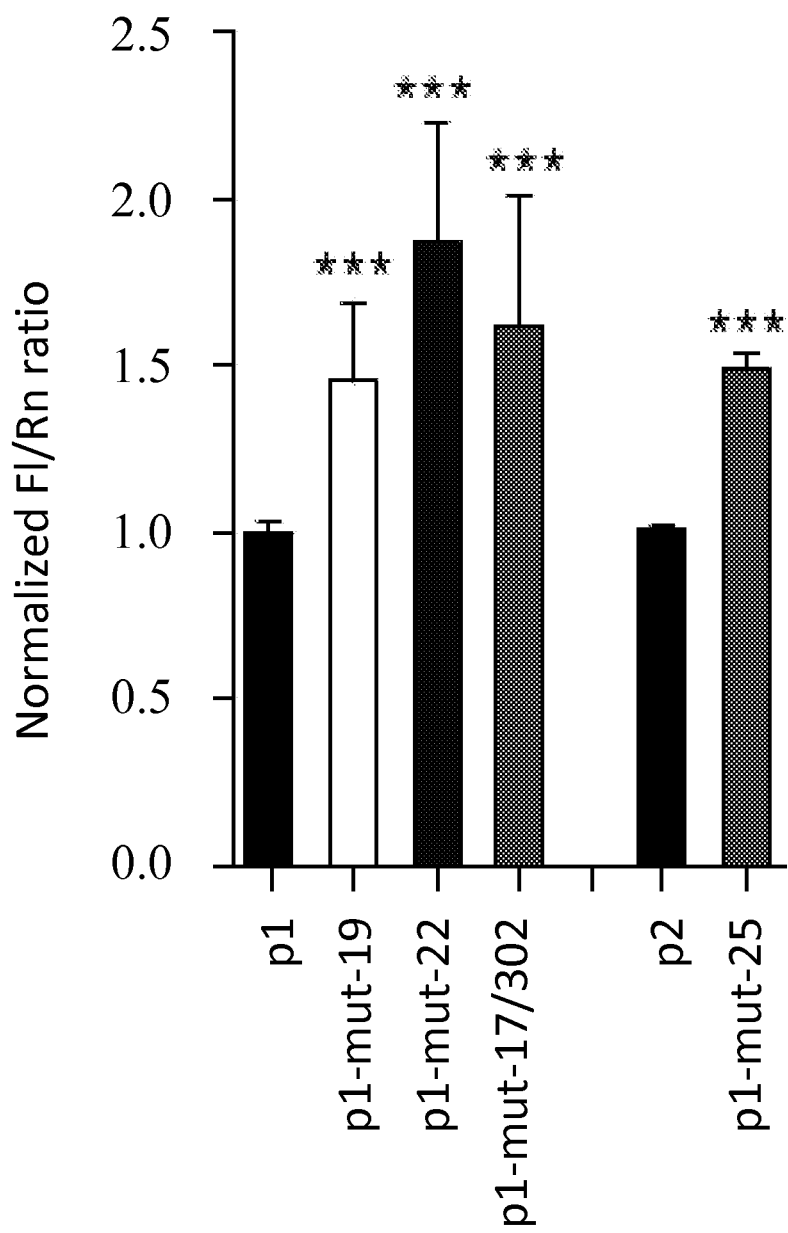

Direct interaction between the tested miRNAs and PTEN mRNA was verified with chimerical luciferase plasmids in which appropriate fragments of the PTEN 3'UTR were cloned downstream of the luciferase reporter gene. This dual-luciferase reporter assay is known in the art. Briefly, DU145 cells were seeded at a density of $6 \times 10^4$ cells per 24-well plate. Twenty-four hours later, 400 ng of p1 or p2 plasmid per well were cotransfected with 80 ng of pRL-TK. Lipofectamine 2000 was used as the transfectant according to the manufacturer's recommendations. Twenty-four hours after transfection, luciferase activity was measured and normalized. FIG. 1E shows wild-type or mutant p1 and p2 reporter plastid ds were transfected into DU145 cells. In this case, mutant refers to mutations engineered in the seed matches, the sequence of the tumor suppressor gene to which the miRNA is suspected to bind. Twenty-four hours after transfection, the luciferase activity of the mutant plasmids was higher than that of the corresponding wild-type plasmids, indicating that the introduced mutations in the seed matches impair miRNA binding to PTEN 3'UTR.

Figure 1F:
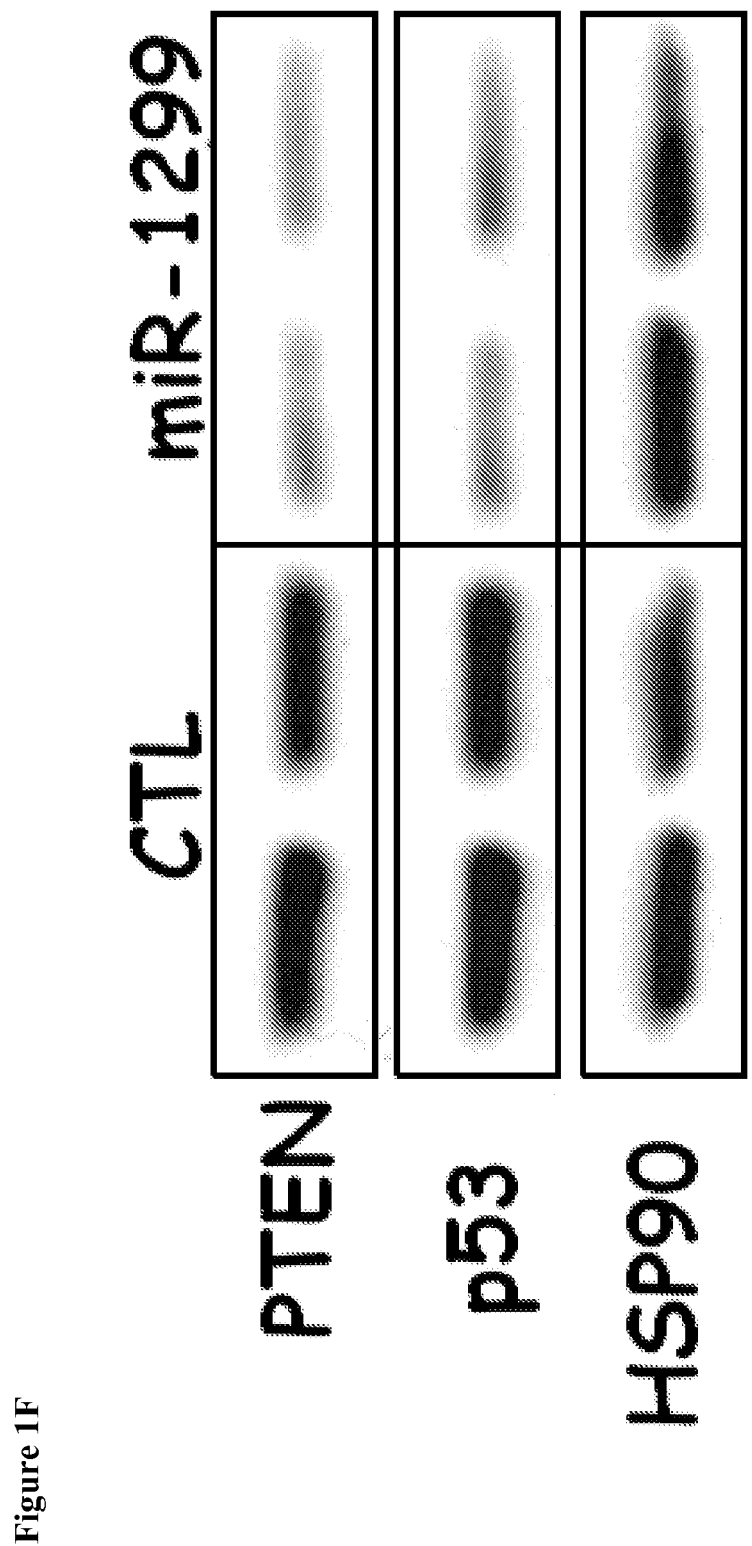
Figure 1F:
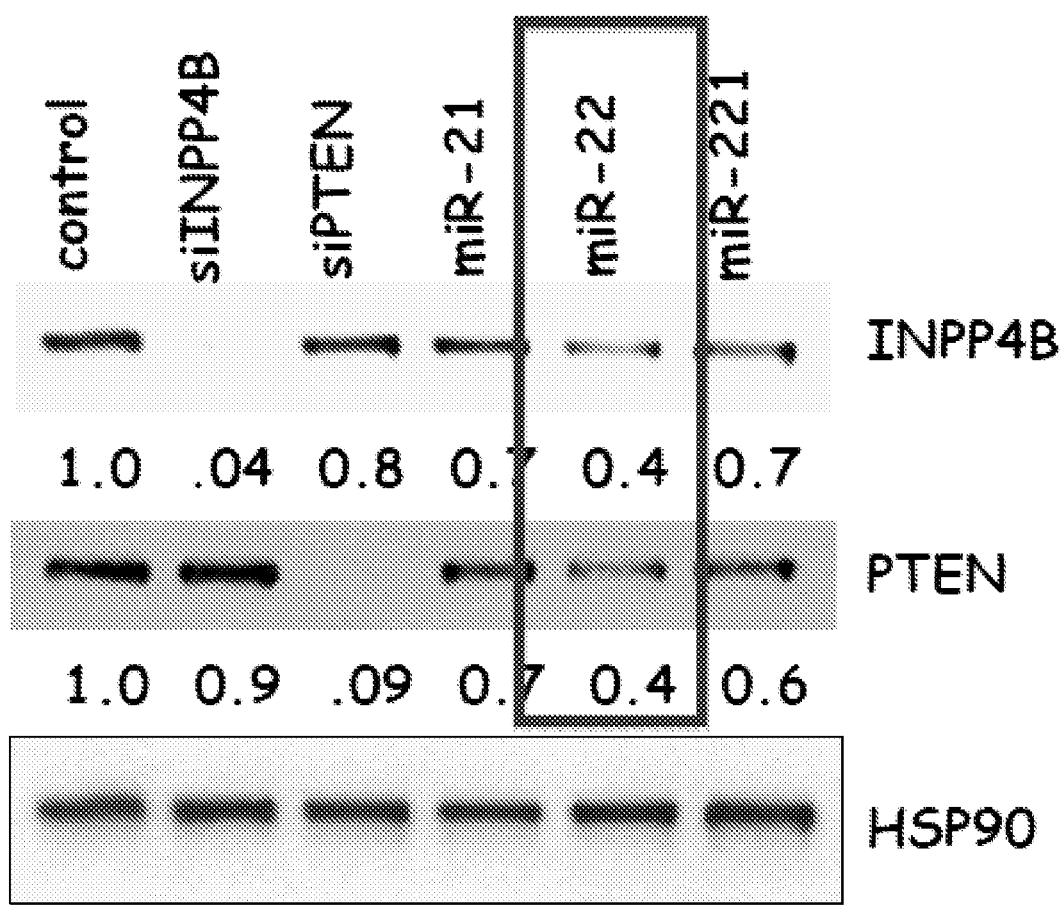
Figure 1F:
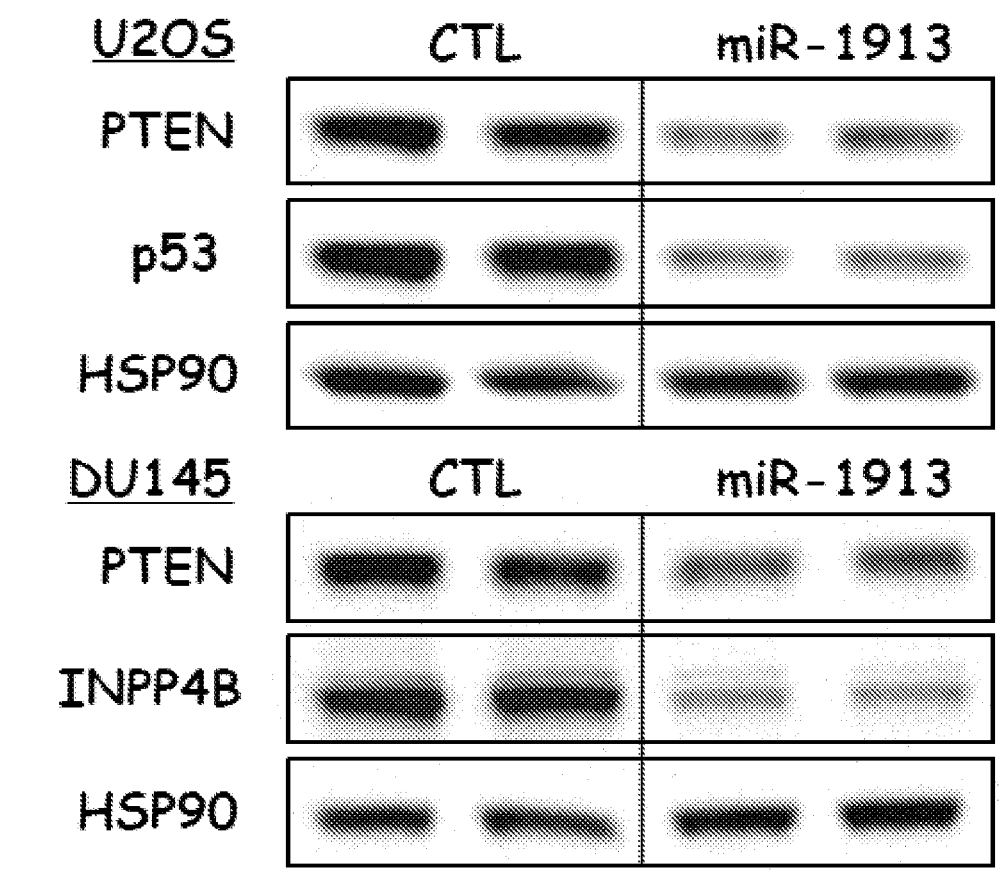

MiRNAs that target further tumor suppressor genes are shown in Table 1 and FIG. 1F. There, miRNAs that regulate either p53 and/or INPP4B are listed. All of these miRNAs regulate PTEN as well as the indicated other tumor suppressor gene (e.g. miR-1299 and others regulate PTEN and p53, while miR-22 and others regulate PTEN and INPP4B). Further, some of these miRNAs regulate PTEN, p53, and INPP4B (e.g. miR-1913, among others).

Figure 2A:
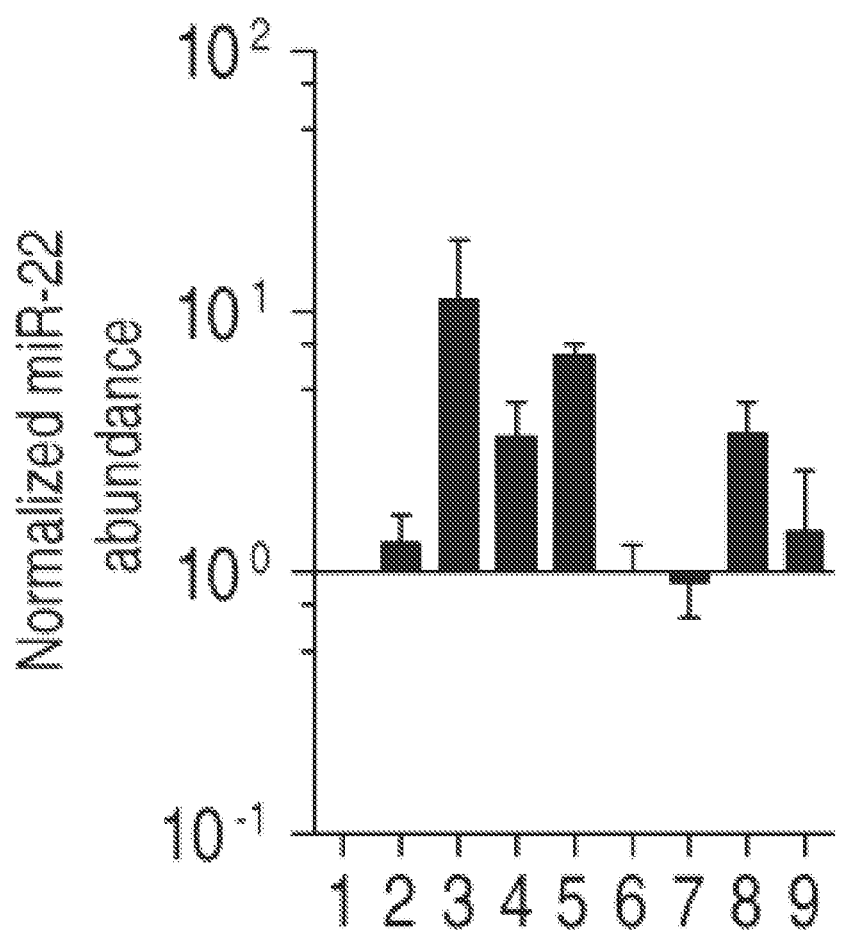
FIG. 2A-FIG. 2D show that tumor suppressor-regulating miRNAs are overexpressed in prostate cancer.
Figure 2B:
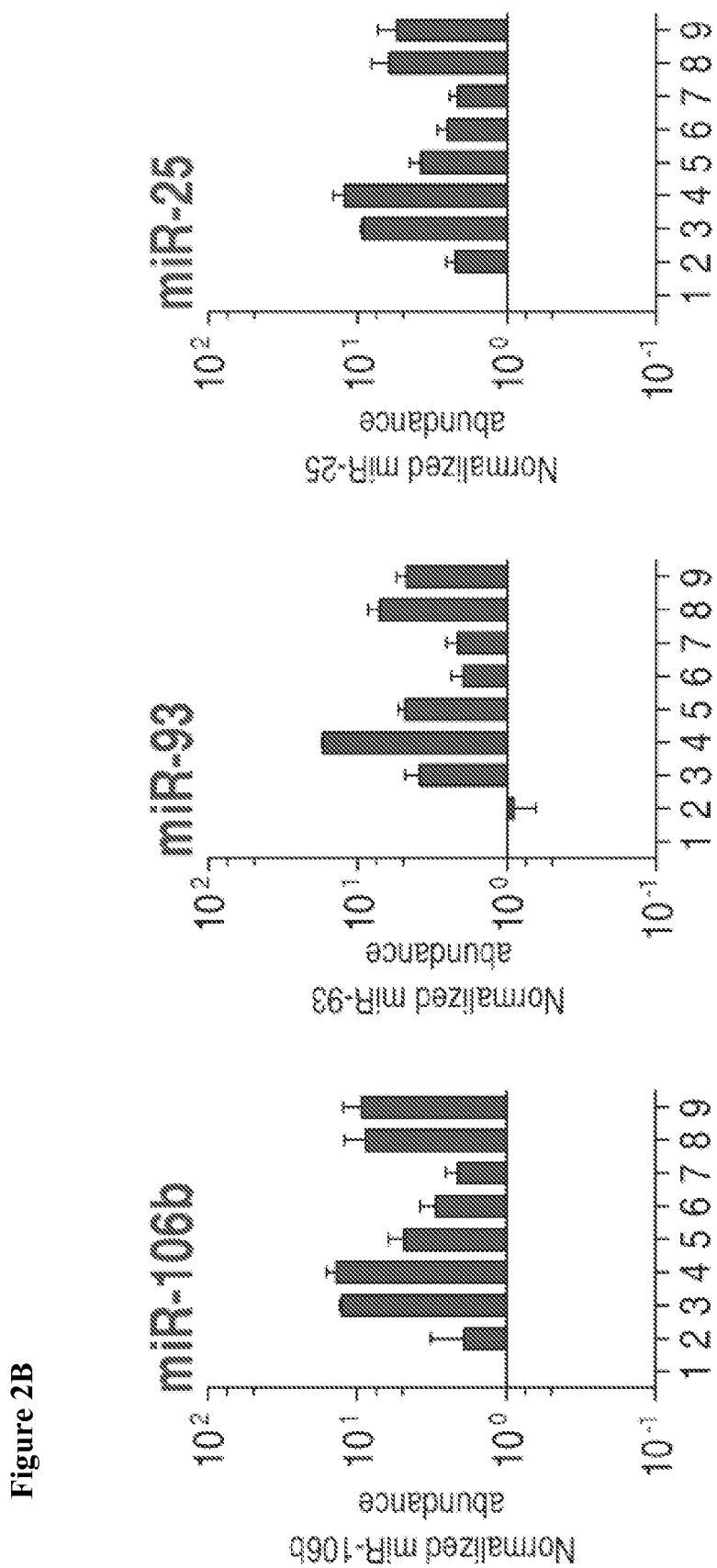
Figure 2C:
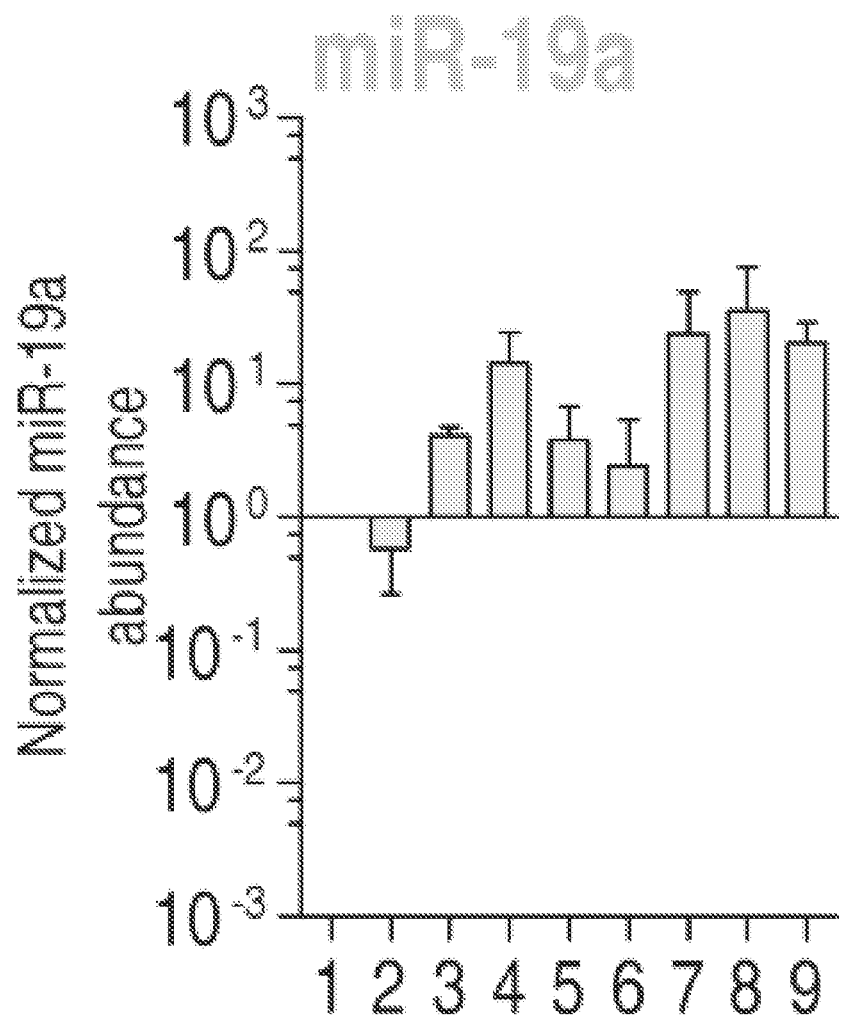

Example 2: Tumor Suppressor-Regulating miRNAs are Overexpressed in Prostate Cancer Real-time reverse transcription polymerase chain reaction (RT-PCR) was performed on a variety of cells: two prostate cell lines derived from normal epithelium, two prostate cell lines derived from primary prostate carcinoma, and five prostate cell lines derived from distant prostate carcinoma metastases. In FIG. 2A-FIG. 2D, the following cells were examined (numbered 1 to 9, in order): RWPE-1 (immortalized normal prostate epithelium), PWR-1E (immortalized normal prostate epithelium), Ca-HpV-10 (primary prostate carcinoma), 22Rv 1 (xenograft of a primary carcinoma), DU145, LnCaP, MDA-PCa-2b, PC3, and VCap (prostate carcinomas metastasized to distal organs). miR-22 was more abundant in both cell lines derived from primary carcinomas and in three of the five metastatic cell lines than in the cell lines derived from normal epithelium (FIG. 2A). A robust increase in the abundance of the three PTEN-targeting components located in the miR-106b-25 cluster (miR-25, miR-93, and miR-106b) was observed in all the prostate cancer cell lines compared to that of the normal cell lines (FIG. 2B). Further, miR-19a (of the PTEN-targeting miR-1792 cluster) abundance was increased in cancer versus normal cells (FIG. 2C).

Figure 2D:
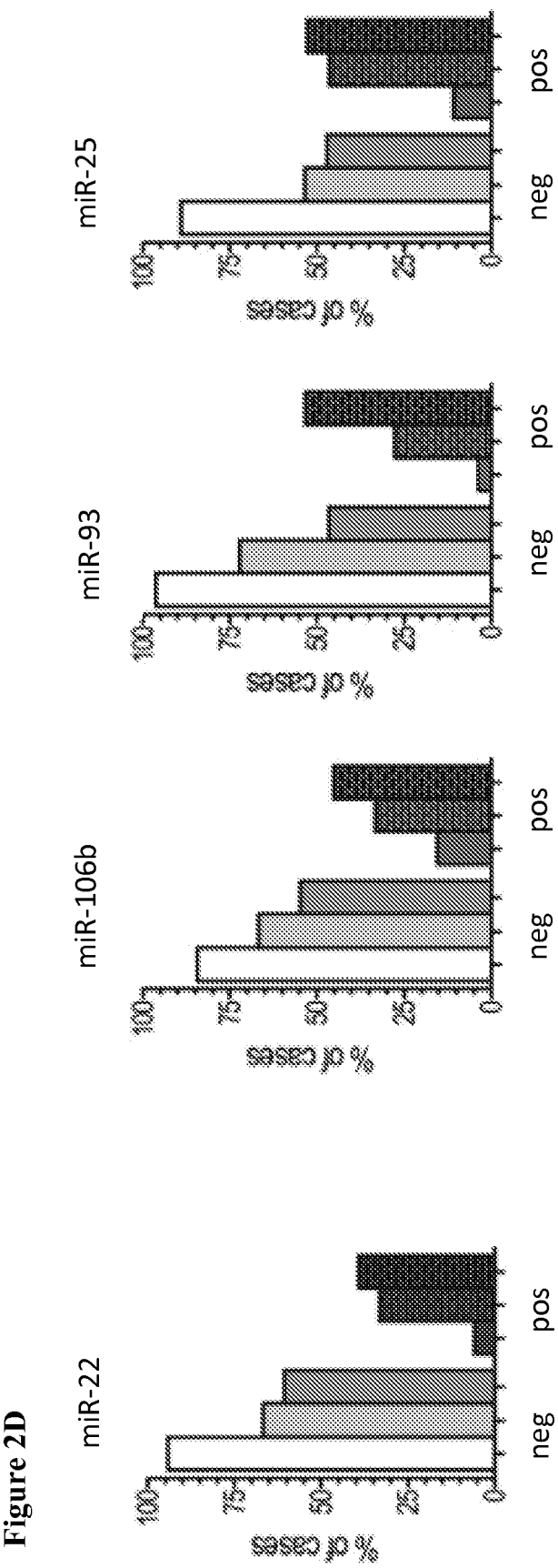

The abundance of miR-22, miR-25, miR-93, and miR-106b in prostate cancer cells was also examined by in situ hybridization (ISH) on a prostate tumor tissue microarray (TMA) containing 184 cases of tumor and matched nontumor tissues. ISH on TMAs was performed on 5-μm paraffin sections with 3' DIG-labeled miRNA LNA (locked nucleic acid) probes with an automatic stainer (Discovery XT, Ventana Medical Systems Inc.). Cells were baked overnight at 60° C., dewaxed, postfixed in 4% paraformaldehyde (PFA) for 12 minutes, and then digested in proteinase K solution (15 μg/ml) for 4 minutes. Hybridization was performed overnight at 22° C. below the melting temperature (Tm) of each probe in a commercial hybridization buffer (RiboHybe, Ventana Medical Systems). Two 16-minute posthybridization washes in 2× SCC were performed at 4° C. above the hybridization temperature. Sections were subsequently incubated for 40 minutes with a biotinylated antibody against DIG (InnoGenex). Detection with streptavidin-alkaline phosphatase and BCIP/NBT (bromochloroindolyl phosphate-nitro blue tetrazolium) substrates was performed for 10 hours with the BlueMap kit (Ventana Medical Systems). A Nikon Eclipse 50i microscope was used for imaging. As shown in FIG. 2D, miRNA abundance was scored for the fractional presence of miR-22, miR-106b, miR-93 and miR-25 in peritumoral tissue (left bars), prostatic intraepithelial neoplasia (PIN; middle bars), and prostate cancer (right bars), as detected by ISH as 0 to 1, negative (neg) or 2 to 4: positive (pos). ISH experiments showed that miR-22, miR-25, miR-93, and miR-106b were absent in most of the nontumor tissue samples, confirming the RT-PCR results in the cell lines derived from normal prostatic epithelium. Up to 53% of the tumor samples were, however, positive for these miRNAs. TMA samples characterized as PIN, an early noninvasive malignant lesion of the prostate epithelium, consistently showed intermediate positively (25 to 45% of positive cases for each miRNA) (FIG. 2D).

Figure 3A:
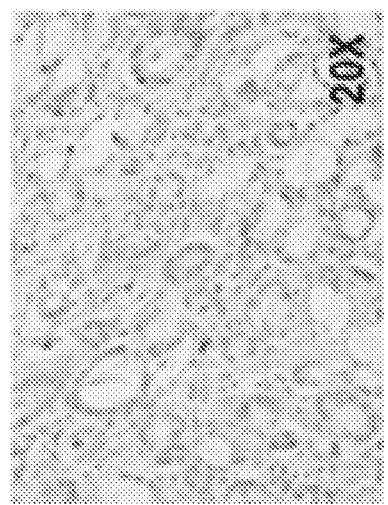
FIG. 3A and FIG. 3B show that the overexpression of tumor suppressor-regulating miRNAs correlates with the overexpression of Dicer.
Figure 3A:
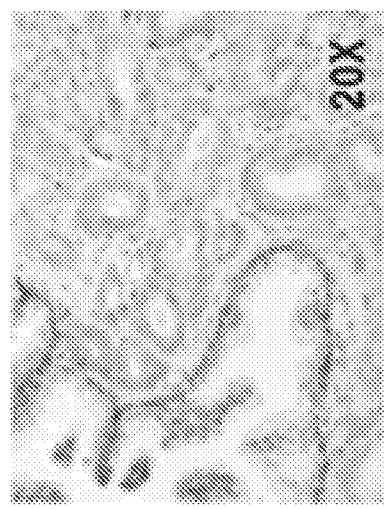
Figure 3A:
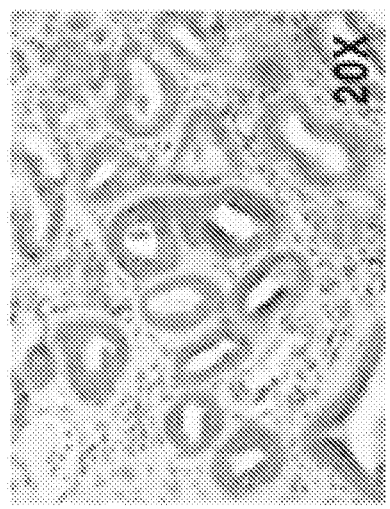
Figure 3B:
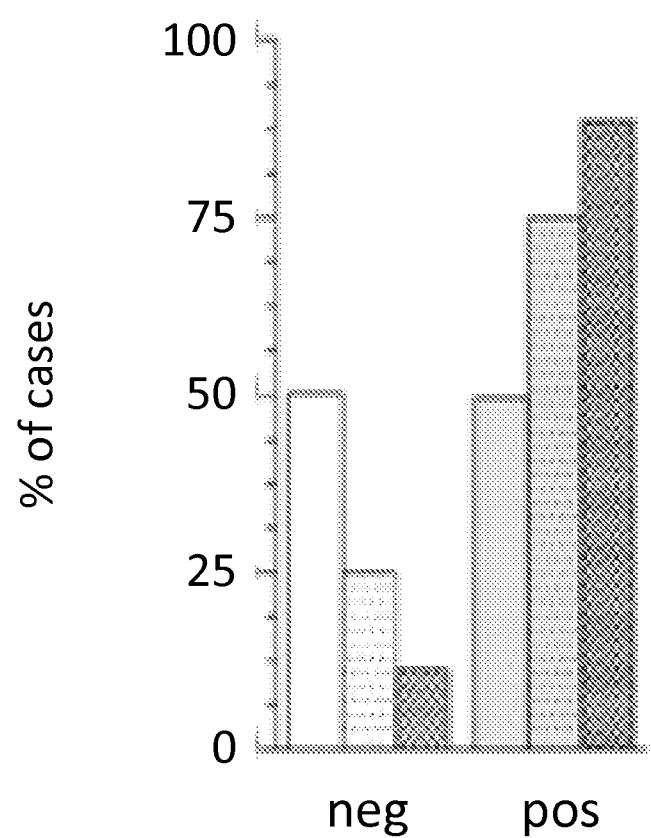

Example 3: Overexpression of Tumor Suppressor-Regulating miRNAs Correlates with Overexpression of Dicer The link between tumor suppressor-regulating miRNAs and cancer was further established by studying the expression of Dicer the enzyme that cleaves pre-miRNAs to release mature miRNAs, by IHC in the same TMA. Increased Dicer abundance was associated with tumor progression (FIG. 3A and FIG. 3B). FIG. 3A shows TMA samples that were considered negative (score: 0) or positive (score: 1 to 2) for DICER by IHC. FIG. 3B shows the presence of Dicer in peritumoral tissues (left bars), PIN (middle bars), and prostate cancer (right bars).

Figure 4A:
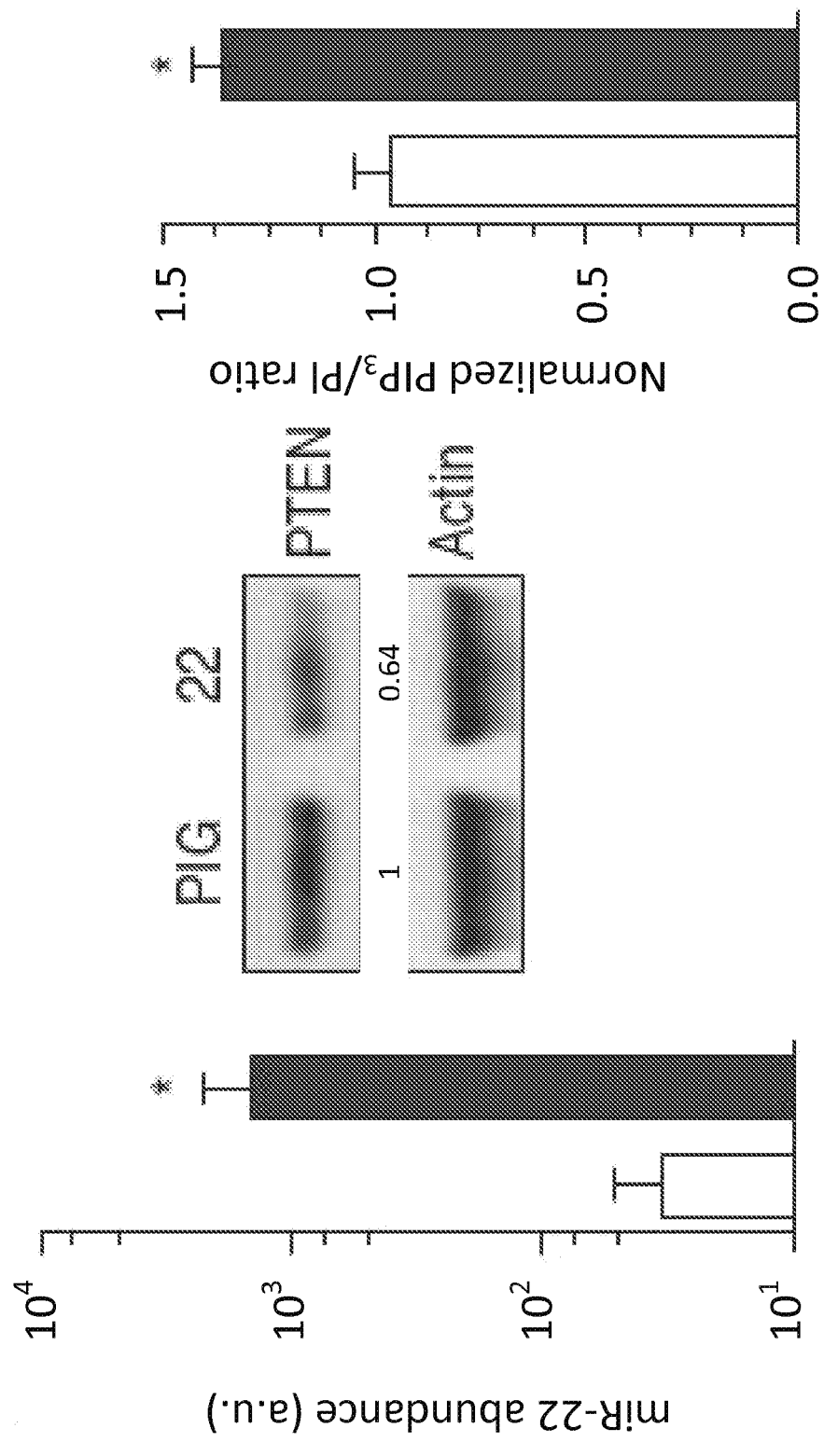
FIG. 4A-FIG. 4E show that tumor suppressor-regulating miRNAs potentiate cell transformation in vitro and in vivo.
Figure 4B:
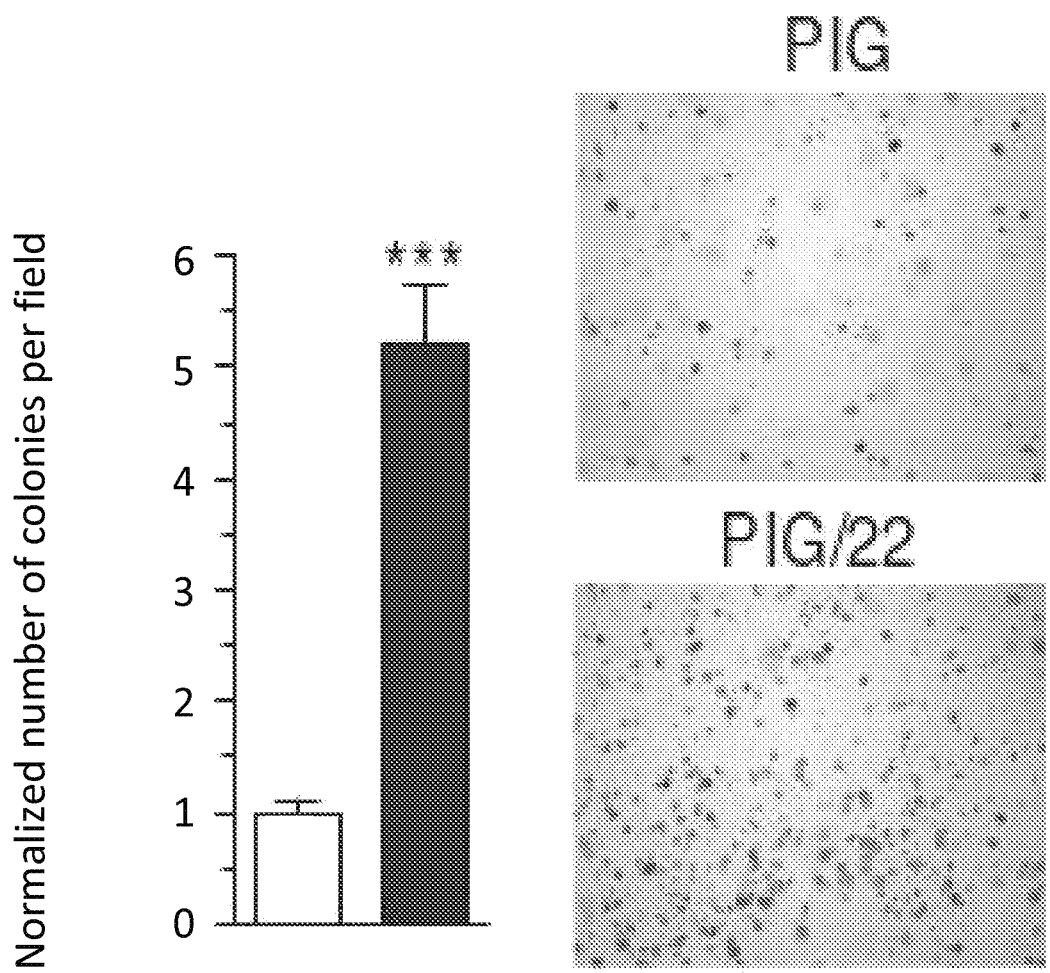
Figure 4C:
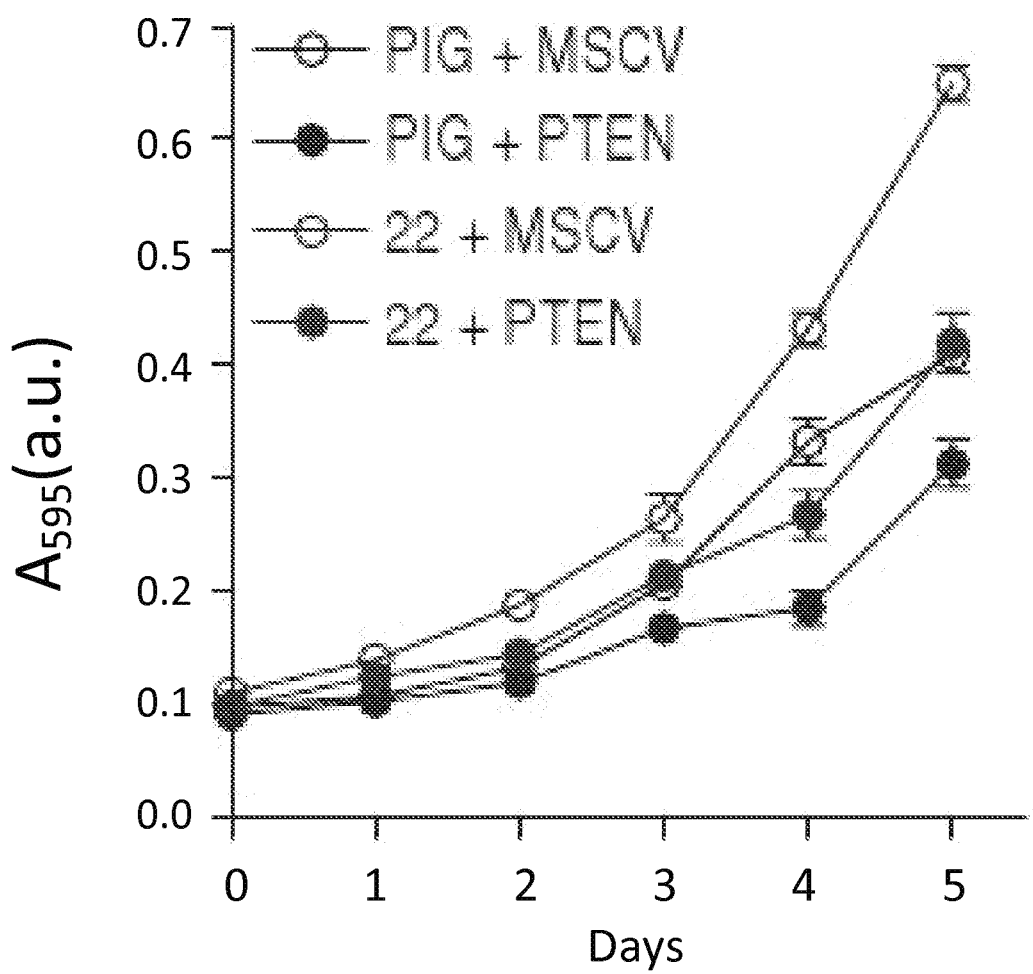
Figure 4D:
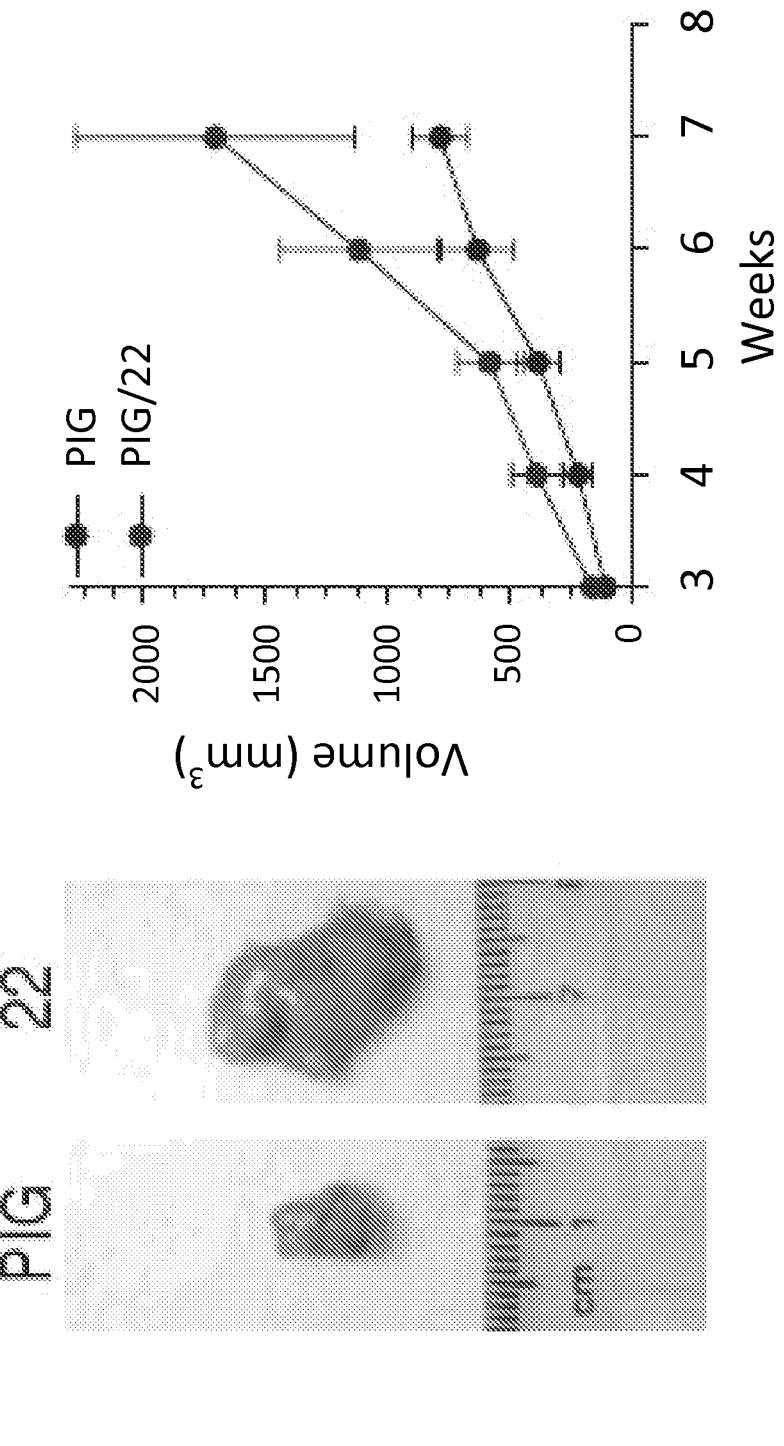
Figure 4E:
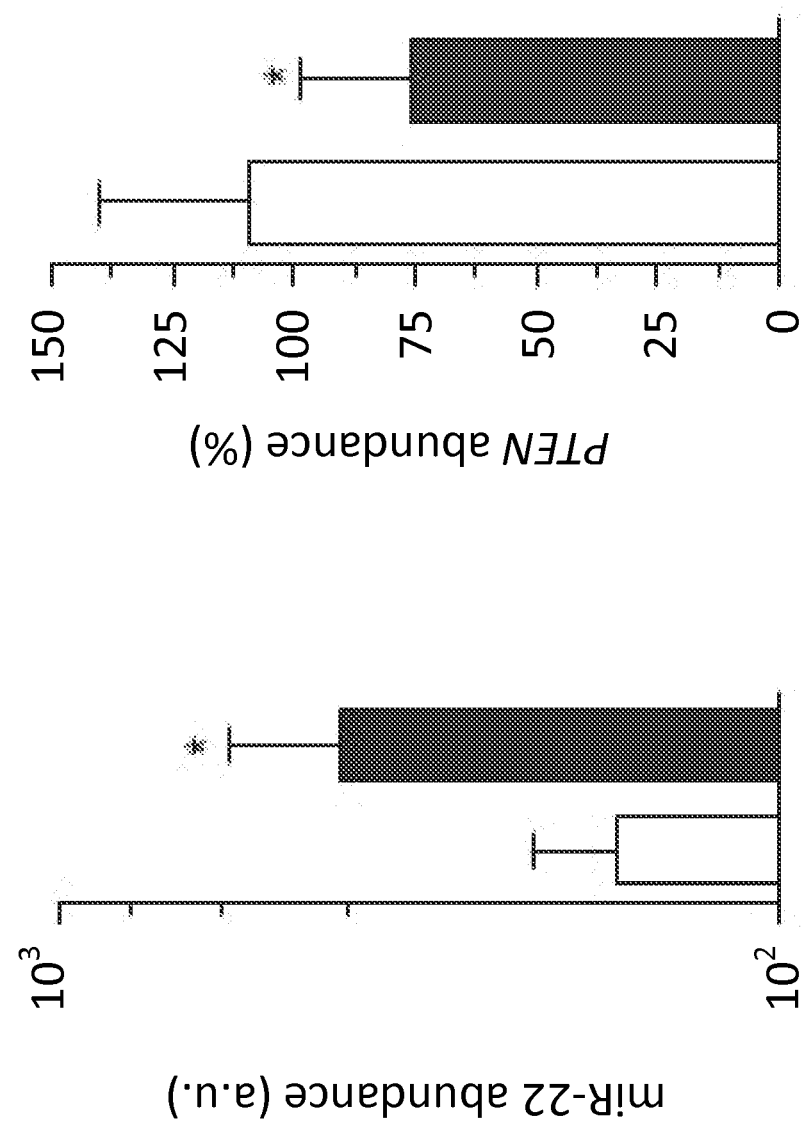

Example 4: Tumor Suppressor-Regulating miRNAs Potentiate Cell Transformation In Vitro and In Vivo The ability of miR-22 to potentiate the proliferation of human prostate cancer cells was examined. DU145 cells that stably expressed a retroviral pri-miR-22 (PIG/22 cells) were generated. PTEN abundance and activity was decreased relative to that of control cells (PIG) (FIG. 4A, showing RT-PCR on the left, Western blot in the center, and PIP3 production on the right). Further, the number of colonies that formed on soft agar was studied for these cells. To do this, a bottom layer was obtained by covering six-well dishes with 3 ml of 0.6% agar in DMEM media. The following day, $5 \times 10^4$ infected cells were plated on this bottom layer in triplicate in 2 ml of 0.3% agar in DMEM with 10% FBS. Colonies were counted after 3 to 4 weeks (DU145) at 40× and 100× magnification. Five fields for each well were counted. A Nikon Eclipse TE300 microscope was used and images were acquired with IPLab software. Cells transfected with miR-22 formed greater numbers of colonies in soft agar compared to control cells (FIG. 4B). To determine whether the effects of miR-22 depended on decreased PTEN abundance, retrovirally transduced DU145 cells with both primiR-22 and PTEN lacking its 3'UTR, so that it could not be targeted by miRNAs, were generated. Exogenous 3'UTR-less PTEN overcame the proliferation-promoting effect of miR-22, indicating that this miRNA depends on PTEN down-regulation to exert its biological activity (FIG. 4C). When injected subcutaneously into the flank of nude mice, PIG/22 cells showed a proliferative advantage, as indicated by their generation of tumors that were twice the size of those generated by PIG-infected cells after 6 to 7 weeks of growth (FIG. 4D). MiR-22 overexpression and the concomitant decrease in PTEN mRNA abundance were confirmed in PIG/22-derived tumors as shown in RT-PCR data in FIG. 4E (left bars are control tumors, right are miR-22 overexpressing tumors).

Figure 5:
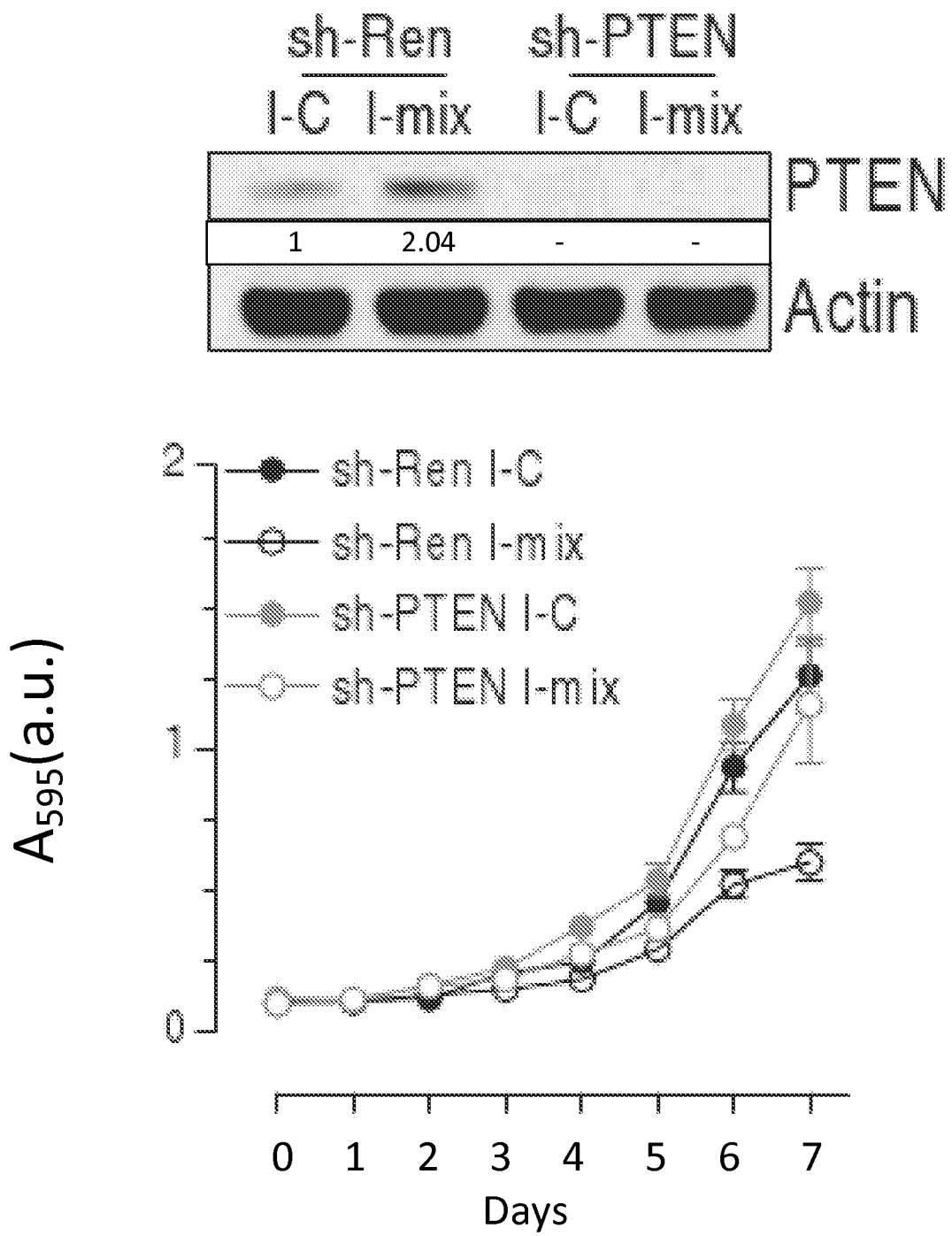
FIG. 5 shows the inhibition of tumor suppressor-regulating miRNAs.

Example 5: Inhibition of Tumor Suppressor-Regulating miRNAs Will Lead to a Reduction or Prevention of Cancers DU145 cell lines stably transfected with short hairpin RNA (shRNA) targeting a control gene Renilla luciferase (sh-Ren) or human PTEN (sh-PTEN) were generated. FIG. 5 shows that when sh-Ren-expressing cells were transiently transfected with a mix of antisense inhibitors of the identified PTEN-targeting miRNAs (I-mix: a combination of antisense inhibitors to miR-19a/22/25/93/106b), PTEN abundance increased and cell proliferation decreased compared to cells transfected with a control miRNA inhibitor (I-C). In contrast, sh-PTEN-expressing cells, which had undetectable PTEN, showed no response to I-mix. This experiment indicates that PTEN-targeting is required by the miRNAs to exert their biological activity. FIG. 5 shows both Western blot and growth curve data.

Figure 6:
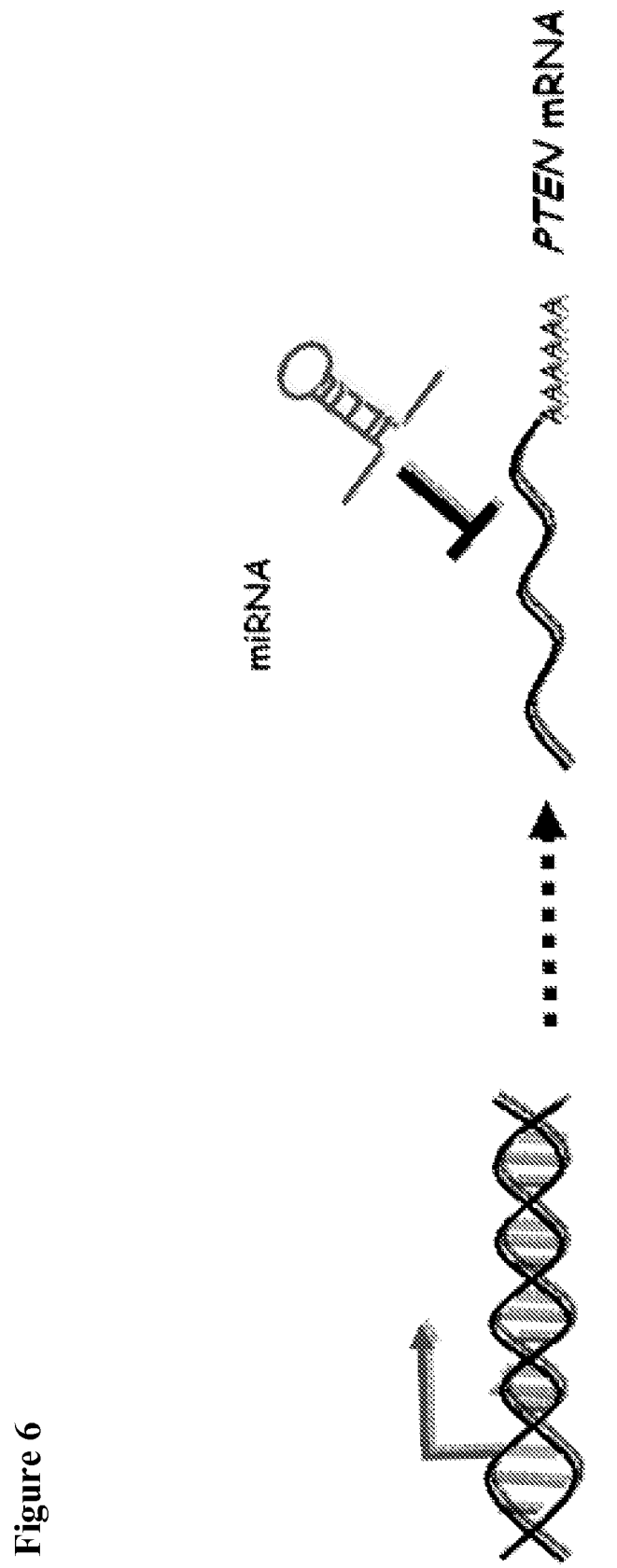
FIG. 6 shows a scheme of the inhibition of tumor suppressor-regulating miRNAs.

Similar studies on other inhibitors of oncogenic miRNAs may suggest further molecules that may be used to treat or prevent cancer. These inhibitors are expected to show positive therapeutic response in prevention or treatment of cancer. Thus, the general model of inhibiting miRNAs that regulate tumor suppressors is expected to be a platform by which to base cancer treatment (See FIG. 6, showing PTEN as an exemplary tumor suppressor).

Example 6: Further Characterization of an Exemplary Tumor Suppressor-Regulating miRNA: miR518c* miR518c* is predicted to target PTEN in the 5'UTR and the protein coding sequence. miR518c* expression is increased in human prostate and colon cancer specimens. Moreover, miR518c* is part of the C19MC cluster on chromosome 19q13, which is amplified in castration resistant prostate cancer and other cancer types. Importantly, miR518c* and PTEN expression are anti-correlated in prostate cancer.

Figure 7A:
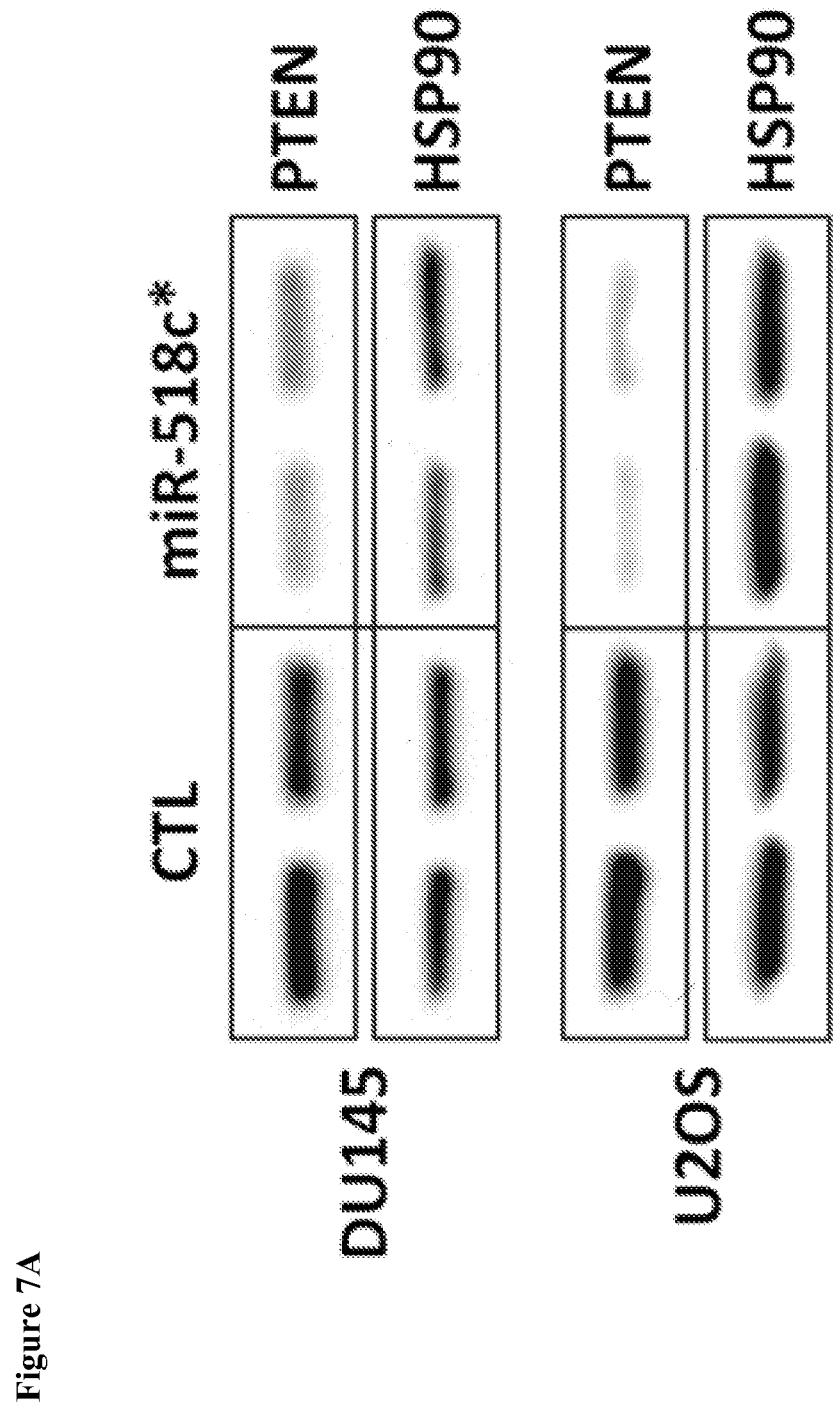
Figure 7B:
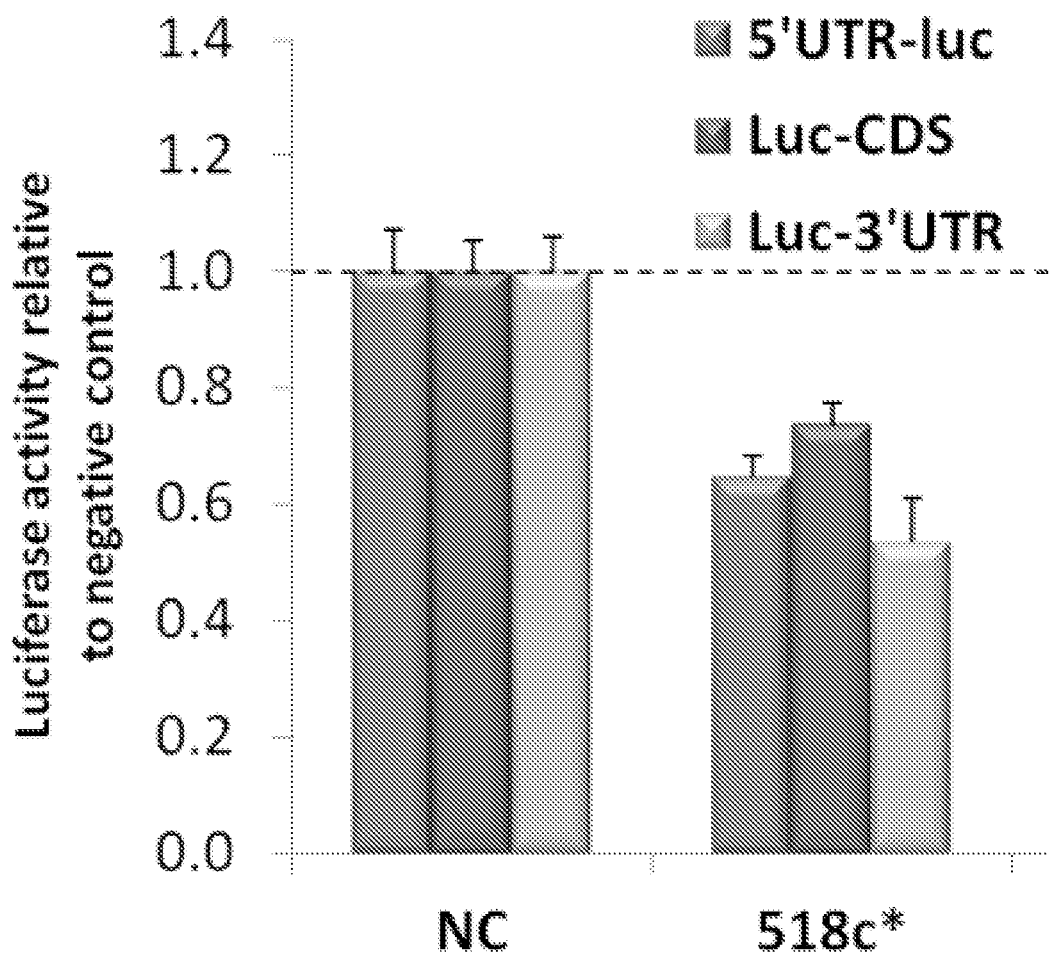

Based on these findings, PTEN was validated as a target of miR518c*. Specifically, FIG. 7A shows Western blot analysis demonstrating that overexpression of miR-518c* results in a significant decrease in PTEN protein levels in both DU145 and U2OS cancer cells relative to the negative control (CTL) transfection. Further, ectopic delivery of miR518c* to prostate cancer or osteosarcoma cells decreased PTEN transcript and protein expression, and concomitantly increased phosphorylation of AKT. miR518c* reduced Luciferase activity of Luciferase-PTEN (5'utr) and Luciferase-PTEN(cds) reporter constructs, indicating direct targeting of PTEN. As shown in FIG. 7B, Luciferase reporter assays demonstrated that overexpression of miR-518c* results in a significant decrease in the activity of PTEN 5'UTR-luciferase (5'UTR-luc), Luciferase-PTEN CDS (Luc-CDS) and Luciferase-PTEN 3'UTR (Luc-3'UTR) reporters relative to the negative control (NC) transfection. Repression of PTEN by miR518c* promotes cell proliferation and anchorage-independent growth in soft agar, suggesting oncogenic properties of miR518c*.

Figure 7C:
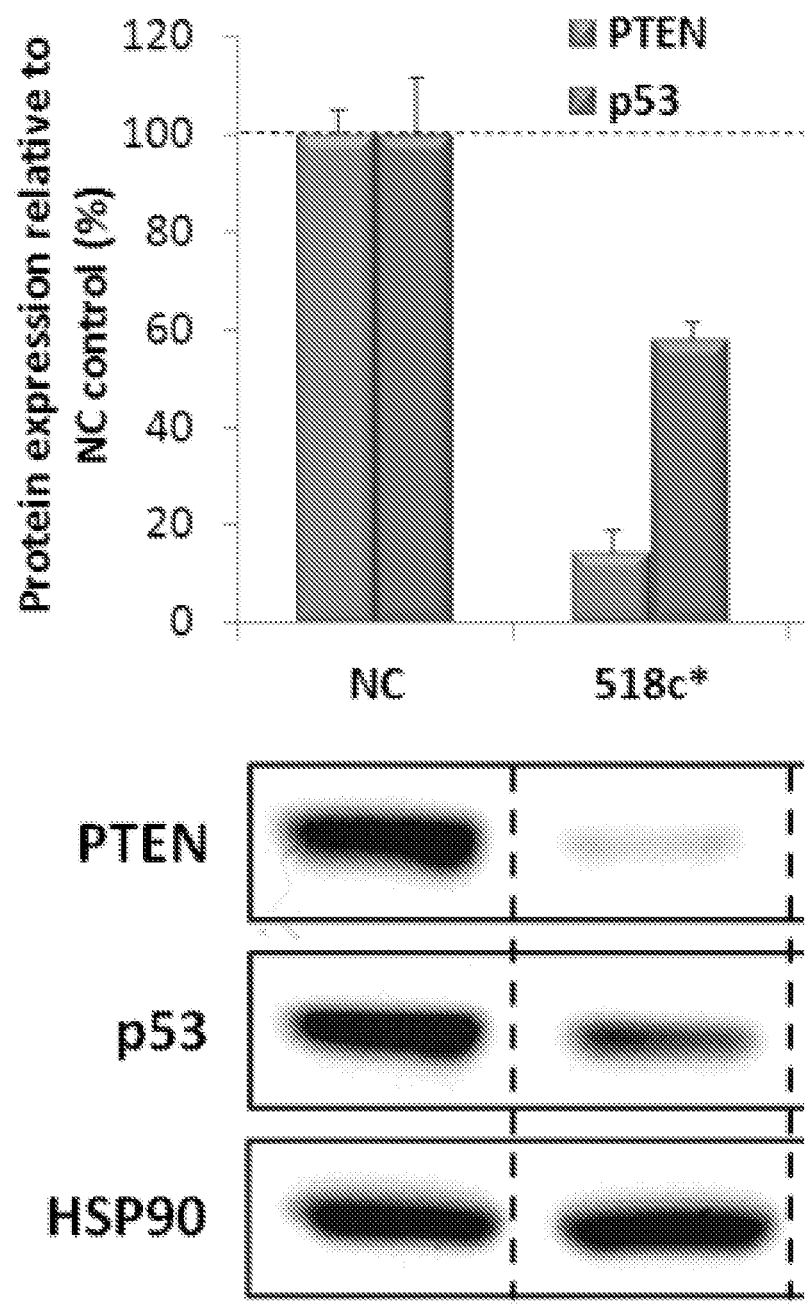
Figure 7D:
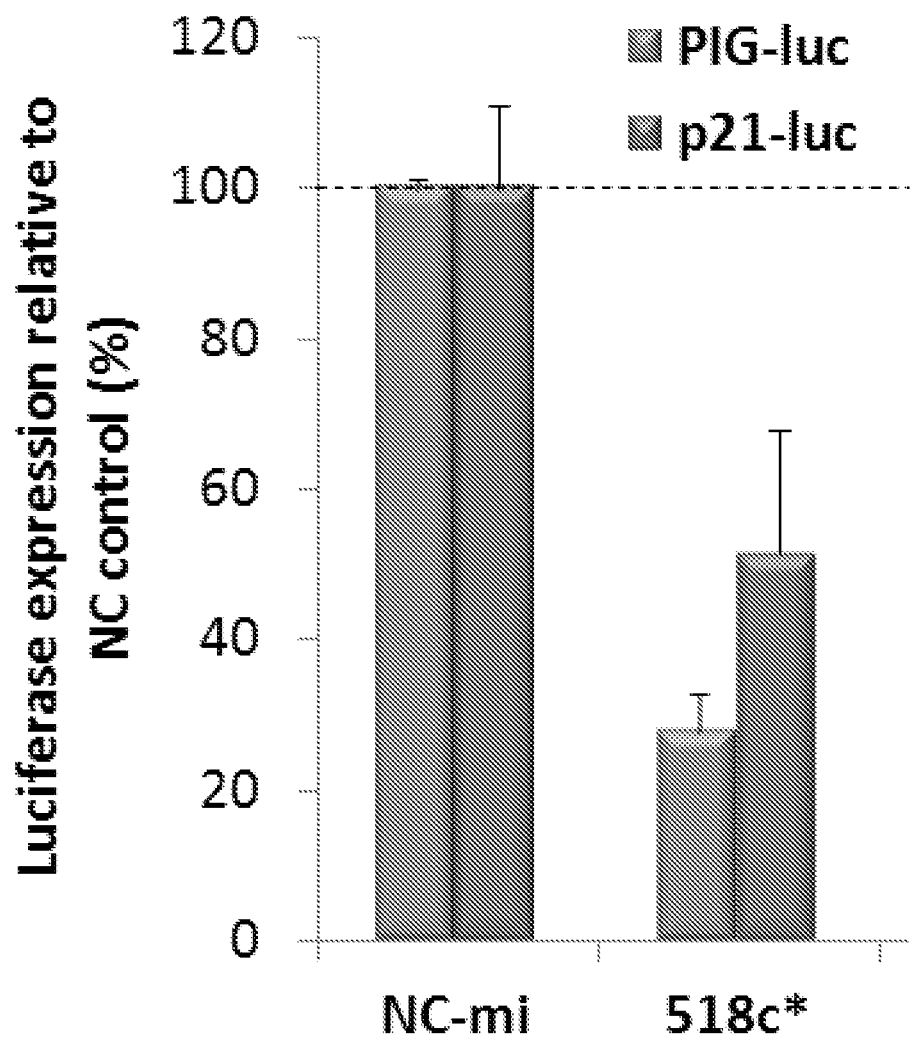

Besides PTEN, additional tumor suppressors were tested as miR518c* targets. Specifically, FIG. 7C shows Western blot analysis demonstrating that overexpression of miR-518c* results in a significant decrease in p53 protein levels relative to the negative control (NC) transfection. Also, delivery of miR518c* to prostate cancer and osteosarcoma cells decreased the expression of p53 and reduced the activity of p53-responsive Luciferase reporter constructs. Specifically, FIG. 7D shows Luciferase reporter assays demonstrating that overexpression of miR-518c* results in a significant decrease in activity of the p53-responsive PIG-luciferase and p21-luciferase reporters.

Figure 7E:
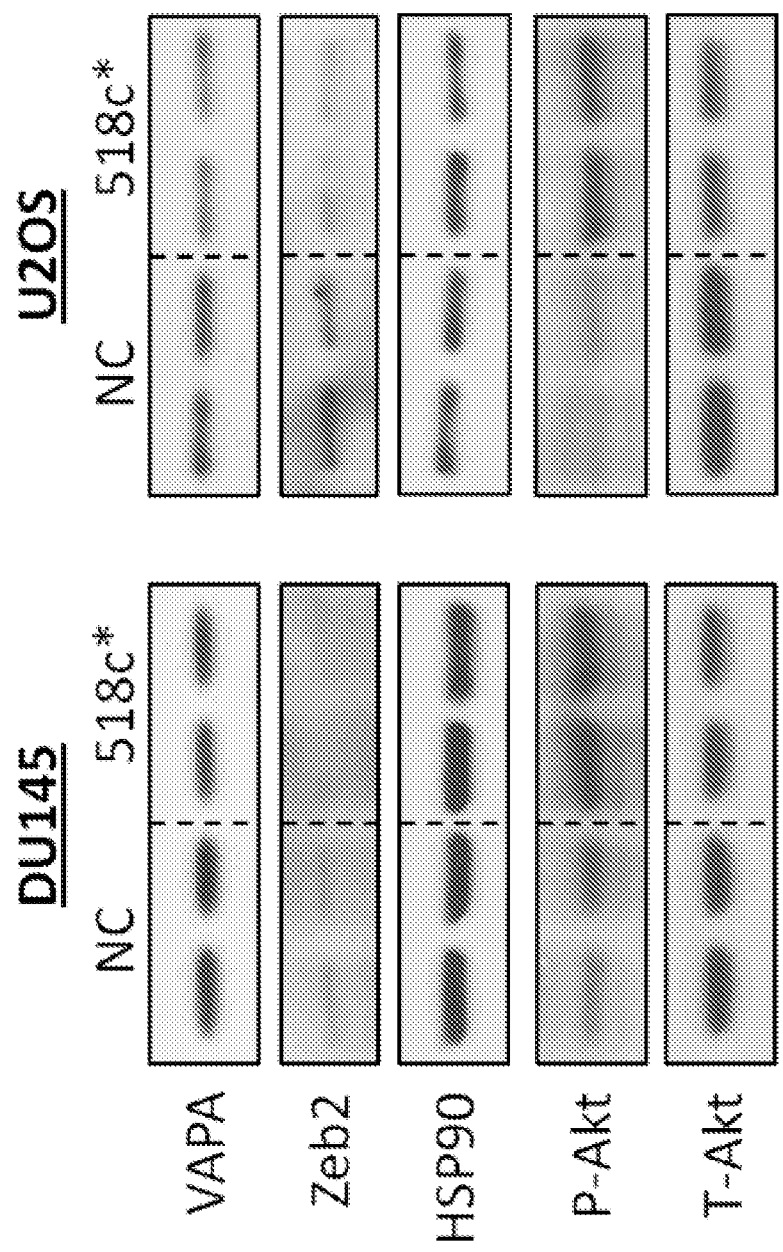

Moreover, miR518c* reduced the expression of the PTEN ceRNAs VAPA and ZEB2. As shown in FIG. 7E Western blot analysis demonstrated that overexpression of miR-518c* results in a significant decrease in protein levels of the PTEN ceRNAs VAPA and Zeb2, and a concomitant increase in the protein levels of Phospho-Akt.

Figure 7F:
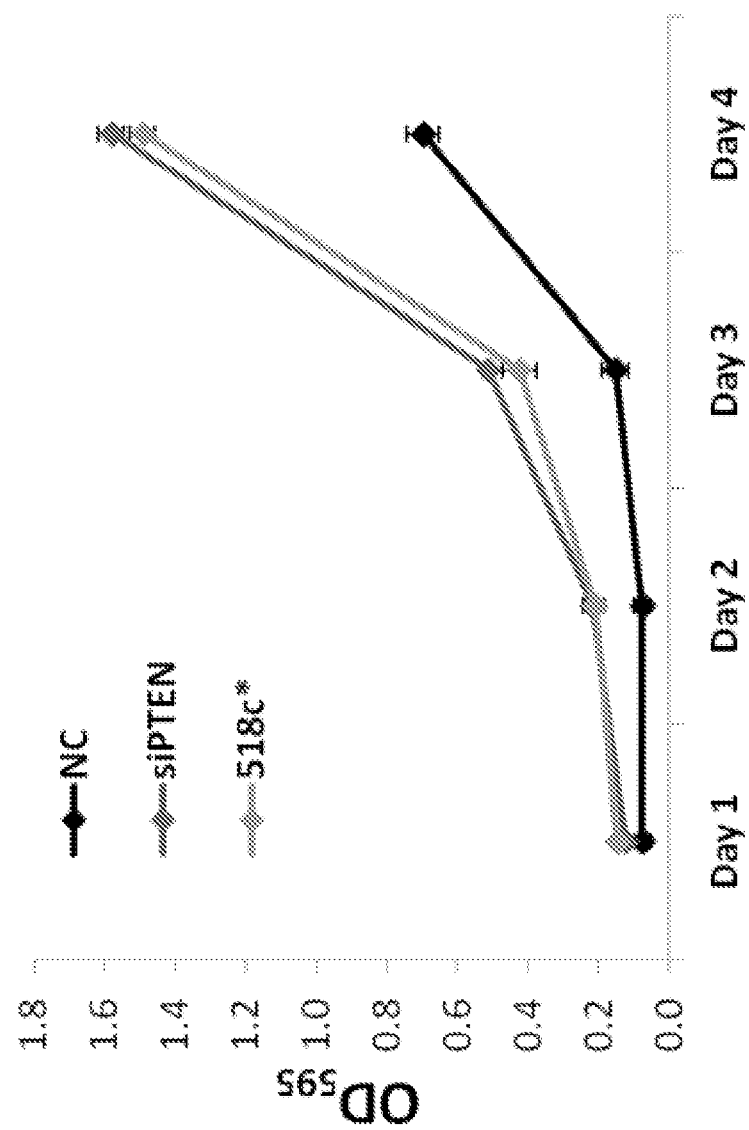

Also, as shown in FIG. 7F, proliferation assays demonstrated that overexpression of miR-518c* results in a significant increase in proliferation of DU145 prostate cancer cells similar to that observed with the PTEN siRNA positive control. And, as shown in FIG. 7G, 518c* expression is significantly elevated in cancer samples in both the GSE21036 prostate cancer dataset and the GSE18392 colon cancer dataset, and it is also significantly anti-coexpressed with PTEN in the GSE21036 prostate cancer dataset.

To investigate the oncogenic potential of miR518c* overexpression in vivo, a transgenic Cags-LSL-miR518c* mouse model was generated. To generate this mouse strain, the genomic fragment containing miR518c* was placed under the control of the Cags promoter and knocked-in into the Cola1 locus. In addition, a loxP-flanked transcriptional stop cassette (LSL) was inserted between the Cags promoter and miR518c*, thus allowing for temporal and spatial control of miR518c* expression by utilization of appropriate Cre mouse strains. High-contribution Cags-LSL-miR518c* chimeras that transmitted the transgene through the germline have been obtained. Cags-LSL-miR518c* mice are being crossed to the EIIa-Cre general deleter strain to investigate the effects of global expression of miR518c*. Cags-LSL-miR518c* mice can also be crossed with tissue-specific Cre strains, such as the prostate-specific Pb-Cre mouse, to assess the oncogenic properties of miR518c* in various tissues.

Figure 8:
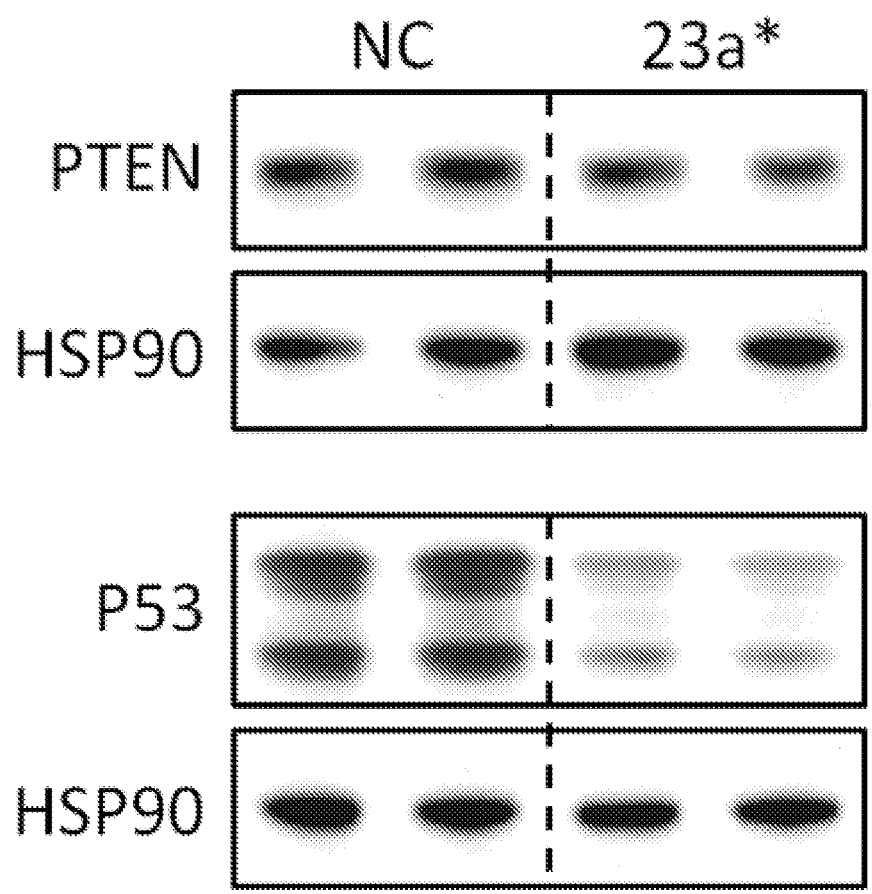
FIG. 8 shows Western blot analysis demonstrating that overexpression of miR-23a* results in a significant decrease in both PTEN and p53 protein levels relative to the negative control (NC) transfection.

Example 7: Further Characterization of an Exemplary Tumor Suppressor-Regulating miRNA: miR23a* miR23a targets both PTEN and p53. Interestingly, the opposite strand of miR23a, miR23a*, also targets PTEN and p53. Indeed, ectopic delivery of the mature miR23a or miR23a* repressed PTEN and p53 protein expression levels. As shown in FIG. 8, Western blot analysis demonstrated that overexpression of miR-23a* results in a significant decrease in both PTEN and p53 protein levels relative to the negative control (NC) transfection.

Moreover, overexpression of a genomic fragment containing miR23a also reduced expression of PTEN and p53, and reduced the activity of Luciferase-PTEN and Luciferase-p53 reporter constructs. Interestingly, miR23a was a 'hit' in a transposon-based forward genetic screen in melanoma in mice, and miR23a levels are elevated in human melanoma metastasis compared to normal melanocytes (data not included).

To investigate the oncogenic properties of miR23a in vivo, Cags-LSL-miR23a mice were generated similar to Cags-LSL-miR518c* mice. The Cags-LSL-miR23a knock-in allele has been transmitted through the germline and the mice are currently being crossed to EIIa-Cre mice. Cags-LSL-miR23a mice can be crossed to tissue-specific Cre mice, such as the melanocyte-specific TyrCreERt2 strain, to investigate tissue specific oncogenic effects of miR23a overexpression.

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention, which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating prostate cancer in a subject in need thereof, comprising:
   (a) obtaining a prostate cancer sample from the subject;
   (b) detecting the decrease of protein expression of both phosphatase and tensin homolog (PTEN) and inositol polyphosphate 4-phosphatase type II (INPP4B) in the sample compared to a non-cancerous cell sample;
   (c) administering to the subject an inhibitor of miR-22, wherein the inhibitor is an oligonucleotide of 8-18 nucleotides in length which binds to miR-22, targets the 3' untranslated region (UTR) of the PTEN gene, and has a sequence that is perfectly complementary to a nucleic acid having the sequence of SEQ ID NO: 12 and wherein: the miR-22 regulates and reduces the protein levels of both PTEN and INPP4B thereby reducing the prostate cancer in the subject.

2. The method of claim 1, wherein the inhibitor is chemically modified.

3. The method of claim 2, wherein the chemical modification is selected from a group consisting of LNA, phosphorothioate, 2'-O-Methyl, 2'-O-Methoxyethyl, 2'-O-alkyl-RNA unit, 2'-OMe-RNA unit, 2'-amino-DNA unit, 2'-fluoro-DNA unit, peptide nucleic acid (PNA) unit, hexitol nucleic acids (HNA) unit, INA unit, and a 2'-O-(2-Methoxyethyl)-RNA (2' MOE RNA) unit.

4. The method of claim 3, wherein the LNA comprises 16 or fewer nucleotides.

5. The method of claim 4, wherein the LNA comprises about 7-8 nucleotides.

6. The method of claim 1, wherein the prostate cancer is metastatic.

7. The method of claim 1, wherein the subject is a mammal.

8. The method of claim 7, wherein the mammal is a human.

9. The method of claim 1, wherein the prostate cancer is non-metastatic.

10. The method of claim 1, wherein the miR-22 increases levels of phosphatidylinositol 3,4,5-trisphosphate ($PIP_3$) in the subject's prostate cancer cells.

* * * * *